(12) United States Patent
Survase et al.

(10) Patent No.: US 10,316,336 B2
(45) Date of Patent: Jun. 11, 2019

(54) SYSTEMS AND METHODS FOR CONTINUOUSLY FERMENTING C5 AND C6 SACCHARIDES

(71) Applicant: API Intellectual Property Holdings, LLC, Minnetrista, MN (US)

(72) Inventors: Shrikant Survase, Thomaston, GA (US); Ryan Zebroski, Fayetteville, GA (US); Georgios Adamos, Thomaston, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 66 days.

(21) Appl. No.: 15/605,930

(22) Filed: May 25, 2017

(65) Prior Publication Data

US 2017/0342444 A1   Nov. 30, 2017

Related U.S. Application Data

(60) Provisional application No. 62/341,683, filed on May 26, 2016.

(51) Int. Cl.
| | |
|---|---|
| C12P 7/10 | (2006.01) |
| C12P 7/04 | (2006.01) |
| C12P 7/16 | (2006.01) |
| C12P 7/28 | (2006.01) |
| C12P 7/52 | (2006.01) |
| C12P 7/54 | (2006.01) |
| C12P 19/02 | (2006.01) |
| C12P 19/14 | (2006.01) |

(52) U.S. Cl.
CPC ............... *C12P 7/10* (2013.01); *C12P 7/04* (2013.01); *C12P 7/16* (2013.01); *C12P 7/28* (2013.01); *C12P 7/52* (2013.01); *C12P 7/54* (2013.01); *C12P 19/02* (2013.01); *C12P 19/14* (2013.01); *C12P 2201/00* (2013.01); *C12P 2203/00* (2013.01)

(58) Field of Classification Search
CPC ............ C12P 7/10; C12P 7/14; C12P 2203/00
USPC ................................................. 435/161, 162
See application file for complete search history.

(56) References Cited

U.S. PATENT DOCUMENTS

2003/0211585 A1* 11/2003 Gaddy .................... C12P 7/065
                                                                                      435/161
2012/0220005 A1*  8/2012 Kumagai ................. C12P 7/10
                                                                                      435/161

OTHER PUBLICATIONS

Collas et al. Simultaneous Production of Isopropanol, Butanol, Ethanol and 2,3-Butanediol by Clostridium Acetobutylicum ATCC 824 Engineered Strains; AMB Express, vol. 2, No. 45, pp. 1-10. (Year: 2012).*
Jeffries et al. Effect of Glucose Supplements on the Fermentation of Xylose by Pachysolen Tannophilus; Biotechnology and Bioengineering, vol. 27, pp. 171-176. (Year: 1985).*
Mu et al. Improved Efficiency of Separate Hexose and Pentose Fermentation From Steam-Exploded Corn Stalk for Butanol Production Using Clostridium Beijerinckii; Biotechnology Letters, vol. 33, pp. 1587-1591. (Year: 2011).*

\* cited by examiner

*Primary Examiner* — Paul C Martin
(74) *Attorney, Agent, or Firm* — O'Connor & Company; Ryan P. O'Connor

(57) ABSTRACT

This invention provides optimized fermentation of cellulosic and hemicellulosic sugars. Biomass-derived hemicellulosic and cellulosic sugars are independently conditioned and separately fermented, utilizing reuse and recycle of microorganisms, metabolic intermediates, and nutrients. Conditioned sugars can be fermented in separate vessels, where excess cells from glucose fermentation are conveyed to hemicellulose sugar fermentation along with raffinate from solvent recovery, to enhance productivity and product yield. Some variations provide a method of fermenting $C_5$ and $C_6$ sugars to fermentation products, the method comprising: fermenting a $C_6$-rich sugar feed to a first fermentation product; fermenting a $C_5$-rich sugar feed to a second fermentation product; removing microorganism cells from the first fermentor, to maintain a cell concentration within a selected range; conveying microorganism cells to a second fermentor; and removing microorganism cells from the second fermentor, to maintain a microorganism cell concentration that is greater than that in the $C_6$-rich fermentor.

23 Claims, 6 Drawing Sheets

SYSTEMS AND METHODS FOR CONTINUOUSLY FERMENTING C5 AND C6 SACCHARIDES

PRIORITY DATA

This patent application is a non-provisional application claiming priority to U.S. Provisional Patent App. No. 62/341,683, filed May 26, 2016, which is hereby incorporated by reference herein.

STATEMENT OF GOVERNMENT RIGHTS

This invention was made with government support under Contract No. DE-EE0006879 awarded by the United States Department of Energy, Office of Energy Efficiency & Renewable Energy. The U.S. government has certain rights in this invention.

FIELD

The present invention generally relates to fractionation processes for converting biomass into fermentable sugars, and conversion of the sugars to organic acids, alcohols (such as butanol), or other fermentation products. The invention also relates to process integration.

BACKGROUND

Biomass refining (or biorefining) is becoming more prevalent in industry. Cellulose fibers and sugars, hemicellulose sugars, lignin, syngas, and derivatives of these intermediates are being used by many companies for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Lignocellulosic biomass presents the vast majority of the sustainable feedstock for sugar-based fermentation. Lignocellulosics include woody and herbaceous material, and residues left behind after forestry and agricultural harvesting and processing. Biomass utilization for sugar recovery is hindered by its recalcitrant nature, resisting deconstruction by most chemicals and microorganisms. Even if the sugars are extracted, they come in a mixture of pentoses and hexoses. Most microorganisms can only utilize hexose sugars, or perform poorly on pentose conversion. Furthermore, the degradation products from harsh pretreatment, or the pretreatment chemicals themselves, are normally toxic to the microorganisms. These impurities can limit the conversion yield, selectivity, and productivity.

Often the rate-limiting step of fermentation is that the product itself inhibits the microorganism (e.g., *Clostridium*) productivity. Furthermore, the fermentation is normally done in a batch process, charging new microorganisms to each batch of sugars. Using membrane technology developed by Toray Industries of Japan, the fermented solvents can be passed through a membrane, where the *Clostridium* is recycled back to the fermentor and the products are sent to downstream purification. Continuous membrane-assisted fermentation enables many fold volumetric productivity enhancement, reducing the cost of fermentors.

Liquid-liquid extraction has been used to recover solutes that have strong solubility into the extractant. Concentrated solute is recovered from the extractant. The liquid-liquid extraction can significantly reduce the energy consumption, compared to traditional distillation. Energy integration and heat recovery can further reduce the energy consumption— making it even less than traditional ethanol production.

*Clostridium acetobutylicum* has been used for industrial production of butanol and acetone since World War I, where acetone was needed for cordite production. By 1950, about two-thirds of the U.S. production of butanol was made by fermentation from starch or molasses (Dodds, 2017). Upon emergence of efficient petrochemical butanol production processes, only a few butanol plants remained in production in the former Soviet Union, Egypt, South Africa, and China until late 20th century. Biomass feedstock was contemplated by the Soviet researchers in the 1960s with mild sulfuric acid to hydrolyze pentoses from agricultural waste (Zverlov et al., 2006). The "continual fermentation" was also established using parallel batteries of 4-8 fermentors improving solvent productivity by 31% over batch fermentation.

Renewed interest in alcohols in the U.S. was driven by elimination of methyl tertiary-butyl ether (MTBE) as an oxygenate in gasoline in 2006 in the U.S., which rapidly was replaced by corn-derived ethanol. Recently two corn ethanol plants in Minnesota have converted to butanol production in the U.S. to produce a higher-value product. The alternative oxygenates including propanol, butanol, pentanol, hexanol and their isomers contain more energy and less oxygen, which allows higher blending in the gasoline. Butanol has a lower blend octane rating than propanol and ethanol. A customized mixture of the alcohols can used to obtain desirable blending characteristics.

The fermentative production of alcohols has only seen incremental productivity improvements. The shortcomings of current biofuel production are well-documented including long biological processing times and energy intensity owing to dilute aqueous solutions. Typical fermentation duration from 24 hours to 72 hours and low titer leads to large industrial fermentation vessels. The long residence times make fermentation susceptible to infection and require sterilization between batches. This further extends the cycle time and reduces capacity utilization. Typical productivity in industrial batch fermentation is between 0.2 and 0.5 g/L/h in fermentation vessels exceeding 1 million liters.

The industrial recovery of ethanol and butanol is being performed almost exclusively using steam stripping. Ethanol feed (to the purification section) contains between 6 vol % and 20 vol % of alcohol, while butanol feed (to the purification section) is only about 2 vol %. This large amount of water must be heated and recycled in the process. The water recycle from corn stillage is commonly accomplished using evaporation, where byproduct dry distillers grains and solubles (DDGS) are recovered. The butanol stillage is much more dilute and anaerobic digestion is typically used for water reuse. Anaerobic digester consumes organic matter and nutrients without providing significant value to the plant. The specific energy consumption of the first-generation product recovery is at least half of the energy contained in the alcohol product, and in the worst case exceeds it.

Lignocellulosic feedstocks, genetic engineering, new process solutions, and design innovations have been suggested to improve sustainability of fermentative processes. However, very little information has been published on the scale-up results and commercialization efforts. Nimcevic and Gapes (2000) published pilot-scale production experience in Austria, where they pointed out that the reliability was one of the reasons that industrial plants utilized batch operation. Butanol production is disadvantaged because of rigorous sanitary requirements, comparative thermal inefficiency, and large amount of water effluent after distillation of product.

Continuous fermentations with enhanced product concentration and productivity have been studied in literature such as continuous chemostat cultures (Gapes et al., 1996), immobilized packed bed reactors (Qureshi et al. 2000; Survase et al. 2012), immobilized fibrous bed reactors (Huang et al., 2002) and membrane-assisted high cell-density continuous cultures (Jang et al., 2013; Tashiro et al., 2005). Tashiro also stated the significance of cell-density control in high-cell-density bioreactors with cell recycling. During the cell recycling, the bioreactor faced a problem controlling the volume of broth in the reactor due to the heavy gas formation and high viscosity.

Fermentors with cell recycling require significant time to build a high cell density. Ferras et al. (1986) reported the requirement of more than 100 hr of cultivation to achieve a cell concentration greater than 20 g/L. To reduce this time, Tashiro et al. (2005) and Zheng et al. (2013) first concentrated the cells of the broth 10 times. A high cell density of approximately 20 g/L was obtained after only 12 h of cultivation by this operation, and the acetone-butanol-ethanol (ABE) productivity increased to greater than 10 g/L/h in short time.

Ni et al. (2013) studied corn stover hydrolysate and cane molasses for butanol fermentation by *C. saccharobutylicum* DSM 13864 in continuous fermentation. They reported that using cane molasses and corn stover hydrolysate as substrate, total solvents of 13.75 g/L and 11.43 g/L were obtained, respectively. The solvent productivities were 0.439 g/L/h and 0.429 g/L/h in a four-stage continuous fermentation continuously operated for 220 hr without compromise in solvent titer.

The use of hemicellulosic spent liquor from $SO_2$-ethanol-water fractionation with supplemented glucose was demonstrated using immobilized packed bed column reactor by Survase et al. (2011). They reported maximum productivity of 4.86 g/L/h with 7.6 g/L total solvents and 0.27 g/g of solvent yield.

Besides an efficient fermentation, the product recovery cost and purification are important to make commercially viable biochemicals. The proposed methods for the recovery of butanol include adsorption (Xue et al., 2016), liquid-liquid extraction (Bankar et al. 2013), gas stripping (Cai et al. 2016), vacuum fermentation (Mariano et al. 2012), and pervaporation (Cai et al. 2017). Integration of solvent recovery can reduce the solvent toxicity significantly and improve the substrate consumption. To overcome the toxicity of the solvents, especially by n-butanol, investigations on the highly selective water-immiscible extractant to remove solvents was shown to increase the solvent titers and yields (Bankar et al., 2012; Bankar et al., 2013). The academic literature proposed several extractants for the butanol extraction including oleyl alcohol, decanol, benzyl benzoate, butyl phthalate (Qureshi and Maddox, 1995, Bankar et al. 2013), 1-dodecanol (Tanakaa et al., 2012), poly(propylene glycol) 1200 (Barton and Daugulis, 1992), castor oil, and oleic acid (Groot et al., 1990). Butyl butyrate, as taught by Melin et al. in WO2015193553, is an extractant with high distribution coefficient, especially for butanol, and low solubility with water.

The addition of acetate and butyrate into the culture media was found not only to enhance solvent production, but also to affect the ratio of acetone/butanol, which might result from the metabolic changes in solvent production (Lee et al., 2008). Gyamerah and Glover (1996) constructed a continuous pilot plant for fermentative production of ethanol, using liquid-liquid extraction to remove the product and recycle the raffinate. They used n-dodecanol as an extractant and immobilized yeast was used to overcome the problem of emulsification. The concentration of byproducts in the fermented broth because of recycle had no adverse effect on the rate of ethanol production. The raffinate recycle allowed higher feed glucose concentration (45.8% w/w) and reported 78% reduction in aqueous purge compared with using a feed containing 10% (w/w) glucose. The effluent recycle after removal of butanol by pervaporation resulted in 101.4% sugar utilization in addition to high productivity of 16.2 g/L/h at a dilution rate of 2.0 per h. A continuous immobilized cell (biofilm) plug-flow reactor with *Clostridium beijerinckii* BA101 was used (Lienhardt et al. 2002).

Improvements are needed in the art, in particular, to deal with low-quality hemicellulose sugars (e.g., $C_5$ sugars) derived from biomass.

SUMMARY

The present invention addresses the aforementioned needs in the art.

Some variations provide a method of fermenting $C_5$ and $C_6$ sugars to one or more fermentation products, the method comprising:

(a) introducing a $C_6$-rich sugar feed and a first nutrient mixture to a first fermentor;

(b) introducing a $C_5$-rich sugar feed and a second nutrient mixture to a second fermentor;

(c) fermenting at least a portion of the $C_6$-rich sugar feed, in the presence of a fermentation microorganism in the first fermentor, to a first fermentation product;

(d) fermenting at least a portion of the $C_5$-rich sugar feed, in the presence of the fermentation microorganism in the second fermentor, to a second fermentation product;

(e) continuously or intermittently removing cells of the fermentation microorganism from the first fermentor, to maintain a first-fermentor microorganism cell concentration within a selected range;

(f) conveying at least a portion of the cells of the fermentation microorganism from step (e) to the second fermentor; and (g) continuously or intermittently removing cells of the fermentation microorganism from the second fermentor, to maintain a second-fermentor microorganism cell concentration within a selected range, wherein the second-fermentor microorganism cell concentration is greater than the first-fermentor microorganism cell concentration.

In some embodiments, maintaining the first-fermentor microorganism cell concentration within a selected range controls foaming in the first fermentor. In these or other embodiments, maintaining the second-fermentor microorganism cell concentration within a selected range controls foaming in the second fermentor.

The method may be operated continuously, in semi-batch, or in batch.

The fermentation microorganism may be a bacteria or a yeast. In some embodiments, the first fermentor is operated aerobically or microaerobically. In these or other embodiments, the second fermentor is operated aerobically or microaerobically.

In certain preferred embodiments, the cells of the fermentation microorganism from the first fermentor are removed with a membrane in step (e). In these or other embodiments, the cells of the fermentation microorganism from the second fermentor are removed with a membrane in step (g).

Step (f) may include conveying fermentation broth containing nutrients from the first fermentor to the second fermentor, with or without cell separation from fermentation broth, whereby the second nutrient mixture is supplemented with additional nutrients (e.g., vitamins, minerals, metabolic intermediates, etc.). In certain embodiments, step (f) includes conveying fermentation broth containing nutrients from the first fermentor to the second fermentor, with or without cell separation from fermentation broth, wherein all of the second nutrient mixture consists of the fermentation broth containing nutrients from the first fermentor.

The first nutrient mixture may be selected to control the first-fermentor microorganism cell concentration. The second nutrient mixture may be selected to control the second-fermentor microorganism cell concentration.

In some embodiments, the selected range of the first-fermentor microorganism cell concentration is from about 10 g/L to about 75 g/L, such as from about 20 g/L to about 50 g/L (cell dry weight per liter of fermentation broth).

In some embodiments, the selected range of the second-fermentor microorganism cell concentration is from about 20 g/L to about 100 g/L, such as from about 25 g/L to about 75 g/L (cell dry weight per liter of fermentation broth). The second-fermentor microorganism cell concentration is maintained or controlled to be greater than the first-fermentor microorganism cell concentration.

The first fermentation product(s) is typically the same as the second fermentation product(s). In principle, due to varying cell density and metabolic shift caused by potentially varying fermentation factors such as nutrient profile, residence time, temperature, and pH, the second fermentation product(s) may be different than the first fermentation product(s) even with the same microorganism present in both fermentors.

The first and second fermentation products may be selected from the group consisting of alcohols, organic acids, polyols, aldehydes, ketones, hydrocarbons, proteins, enzymes, and combinations thereof.

In some embodiments, the first and second fermentation products include a combination of acetone, n-butanol, and ethanol; a combination of isopropanol, n-butanol, and ethanol; or a combination of acetone, isopropanol, n-butanol, and ethanol.

The first and second fermentation products may include one or more $C_2$-$C_8$ alcohols, such as various isomers of butanol, pentanol, or hexanol.

The first and second fermentation products may include one or more acids selected from the group consisting of acetic acid, butyric acid, lactic acid, succinic acid, and combinations thereof.

DETAILED DESCRIPTION OF SOME EMBODIMENTS

Figure 1:
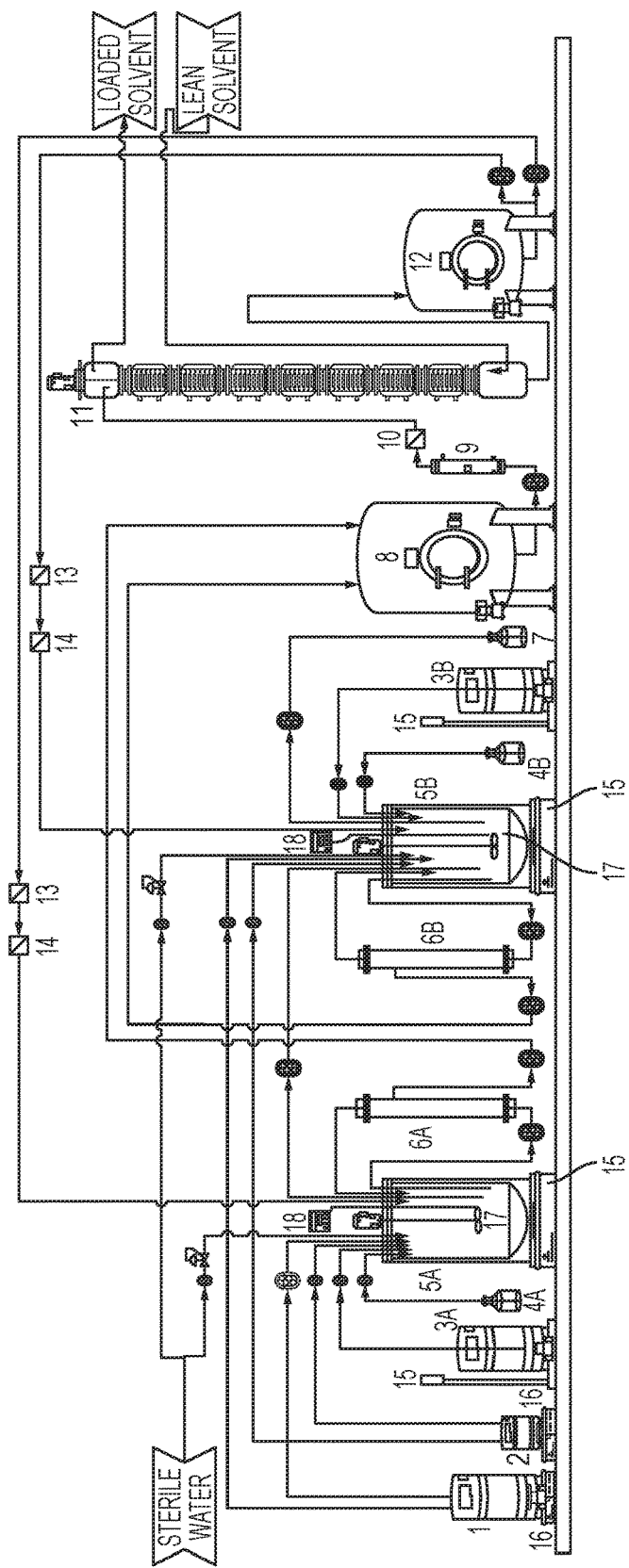
FIG. 1 is a schematic diagram of a membrane cell-recycle bioreactor system used for high-cell-density continuous fermentation, in some embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The invention relates to the actions of microorganisms in bioreactors to convert saccharides (sugars) to form chemical products, aerobically or anaerobically. In this specification, the term "fermentation" will refer to the action of any microorganism in any bioreactor to produce any biochemical product, which is consistent with the common industrial use of the term. As such, fermentation herein is not limited to the strict formal definition of the action of a microorganism in the absence of oxygen.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

Some variations of the invention are premised on the recognition of several significant problems, as follows.

1) There is often limited conversion and slow rate of conversion of $C_5$ saccharides during the continuous fermentation of mixed $C_5/C_6$ saccharide solutions, due to the preferential consumption of $C_6$ saccharides (usually glucose), when present. The continuous feed of high levels of $C_6$ saccharides allows the organism to continue to consume largely $C_6$ saccharides, and limits the extent to which $C_5$ saccharides (or $C_6$ saccharides other than glucose) will be consumed.

2) The creation of large amounts of relatively dense foam suspends some of the microorganisms in the foam. This limits the transport of substrate and nutrient to the organism, and transport of metabolic products away from the organism. These stress factors result in a deteriorated organism performance, and/or the production of undesirable byproducts, and/or death of the organism. The foam also poses a process problem, in that it normally must be controlled either mechanically, or by means of the addition of antifoam.

3) The age distribution of the microorganism population usually needs to be controlled. For some organisms, the productivity of the organism decreases as the organism ages, resulting in less of the desired product(s) being produced per kg of substrate consumed. Furthermore, the selectivity of the products produced can change, resulting in less of the desired product(s) being formed per kg of substrate consumed. The organisms can also produce metabolic byproducts that affect the performance of other organisms.

4) The optimal cell density (g DCW/liter fermentation broth), also referred to herein as cell concentration, depends on the incoming sugar profile. In particular, the cell concentration required for the effective and efficient conversion of hydrolysates containing high concentrations of fermentation inhibitors and/or fermentations of high concentrations of saccharides other than glucose, is often higher than that required for the effective and efficient conversion of hydrolysates containing low concentrations of fermentation inhibitors and/or high concentrations of glucose. The maintenance of a higher cell concentration alters the viscosity, surface tension, and other physical properties of the fermentation broth, resulting in a greater tendency to form stable foam (see problem 2, above). Growth and maintenance of excessive cell mass also reduces the amount of substrate available for the production of the desired fermentation products.

One manifestation of the invention involves the continuous fermentation of two saccharide streams, in parallel. The first fermentation system (membrane-assisted or otherwise) processes a sugar substrate having low inhibitor concentration and/or high glucose concentration. The cell concentration is controlled to provide the productivity needed, and at the same time is limited to a value that prevents the undesirable foaming described above in key problems 2 and 4. The limitation of the cell concentration may be achieved by (i) a purge of cells (continuous or intermittent) from the first fermentation system into a second fermentation system, and/or (ii) an application of fermentation nutrient specifically designed to maintain the desired cell concentration for the first fermentation system.

The second fermentation system (membrane-assisted or otherwise) processes a sugar substrate having high inhibitor concentration and/or low glucose concentration. The cell concentration is controlled at a higher value (compared to the first fermentor) to provide the productivity needed, and at the same time is limited to a value that prevents the undesirable foaming described above. The limitation of the cell concentration may be achieved by (i) a purge of cells (continuous or intermittent) from the second fermentation system into a disposal system, or another fermentation system, and/or (ii) an application of fermentation nutrient specifically designed to maintain the desired cell concentration for the second fermentation system.

The fermentation of $C_5$ saccharides can be carried out separately from those of $C_6$ saccharides. This allows the organism to activate and utilize the pathways necessary for the efficient conversion of $C_5$ saccharides. The cell density can be controlled at a level that is appropriate for each fermentor. High-productivity $C_6$ saccharide fermentations can be run with a relatively low cell density to limit foaming, and minimize the amount of substrate that is converted to biomass, as well as maintain a healthy population age distribution. Lower-productivity $C_5$ saccharide fermentations can be run with a higher cell density, allowing for the efficient and effective conversion of $C_5$ substrate in the presence of high inhibitor levels and/or difficult-to-ferment $C_5$ saccharides (or non-glucose $C_6$ sugars derived from hemicellulose, such as mannose or galactose). The cells purged from the first fermentation system, and the contents (e.g., product, nutrients, metabolic intermediates, etc.) in the fermentation broth of the first fermentation system, are reused or recovered in the second fermentation system.

The present inventors utilized an integrated pilot scale system shown in FIG. 1 to produce a mixture of solvents (fermentation products) from conditioned cellulosic and hemicellulosic sugars. FIG. 1 is a schematic diagram of a membrane cell-recycle bioreactor system used for high-cell-density continuous fermentation to produce n-butanol and other products. The elements of FIG. 1 are as follows:

1: Nutrient tank
  2: Growth nutrient tank
  3A: $C_6$ Hydrolysate tank
  3B: $C_5$ Hydrolysate tank
  4A: C6 fermentor aqua ammonium hydroxide
  4B: $C_5$ fermentor aqua ammonium hydroxide
  5A: $C_6$ fermentor
  5B: $C_5$ fermentor
  6A: $C_6$ fermentor UF membrane
  6B: $C_5$ fermentor UF membrane
  7: Cell purge tank
  8: Permeate tank
  9: Aqueous feed (to extraction column 11) heat exchanger
  10: Aqueous feed (to Extraction Column 11) check filter 11: Forward extraction column
12: Raffinate tank
13: Raffinate pre-filter
14: Raffinate sterile filter
15: Weight scale
16: Tank magnetic agitator
17: Tank agitator
18: pH probe and transmitter Lignocellulosic materials from mechanical, thermal, chemical, or biological pretreatment, or any combination thereof, in which cellulose and hemicelluloses are liberated, may be used for sugar feedstocks. Polymeric sugars should be substantially hydrolyzed to their monomeric form. Separated fractions consist mainly of glucose and a mixture of xylose, arabinose, mannose, and galactose, depending on the starting feedstock. The glucose fraction should contain glucose at over 80% of the total sugars, and preferably about 85%, 90%, or more. The hemicellulosic sugars should not contain more than 50% of glucose, such as less than about 40%, 30%, 20%, 10%, or 5% glucose (i.e. on a sugar basis).

Each fraction is separately conditioned to have a desired level of other biomass components and pretreatment side products. The conditioning includes unit operations from the group of chemical precipitation, physical separation, membrane filtration, ion exchange or exclusion, and activated carbon treatment. The conditioning preferably reduces soluble inhibitors about 50% or more, while retaining 90% or more of sugars and beneficial components. The inhibitors include lignin-derived components, sugar degradation products (e.g., furfural), acids, and high-molecular-weight extractives. In particular, formic acid and soluble lignin inhibit bacterial fermentation. On the other hand, acetic acid from hemicelluloses is a beneficial intermediate in the butanol fermentation.

Some variations utilize the system of FIG. 1 as follows. The conditioned glucose sugars are stored in tank 3A and used to propagate microorganism by providing growth nutrient from tank 2. The propagated seed culture is transferred or retained for initial batch fermentation in vessel 5A until most of the glucose is consumed. Nutrients from tank 1 and ammonia 4A are fed to maintain fermentation conditions. After an initial batch period, the cell density is at least doubled, or preferably increased to about 10-fold using selective membrane 6A, while permeate is removed for solvent recovery 8. The cell density is important to reach high solvent productivity while continuously feeding glucose-rich hydrolysate to the first fermentor 5A. The cell density in the first fermentor is maintained by conveying cells to the second fermentor 5B, which receives continuously conditioned hemicellulosic sugars from tank 3B. When glucose in the feed to hemicellulosic fermentor 5B is maintained low, the hemicellulosic hydrolysates from storage 3B are fed continuously for consumption by the microorganism. The second fermentor 5B also utilizes metabolic intermediates and nutrients in the transfer from the first fermentor 5A. The second fermentor content is continuously recycled through an independent membrane 6B to reach and maintain desired cell density. Upon reaching desired cell density in the second fermentor, excess cells are purged for disposal 7, in this example. The membrane-assisted continuous fermentation with cell recycle and inter-fermentor transfer is continued. Meanwhile, the fermentation products are extracted from the aqueous permeate 8 through temperature control 9 using an immiscible extractant, such as butyl butyrate. The aqueous raffinate 12 is recycled from liquid-liquid extraction column 11 back to fermentor dilution. The water is recycled though sterile filters 13 and 14 to avoid voluminous waste treatment and returns unused sugars, nutrients and metabolic intermediates to fermentation. The extractant is stripped off from the fermentation products and returned to extractor 11.

Figure 2A:
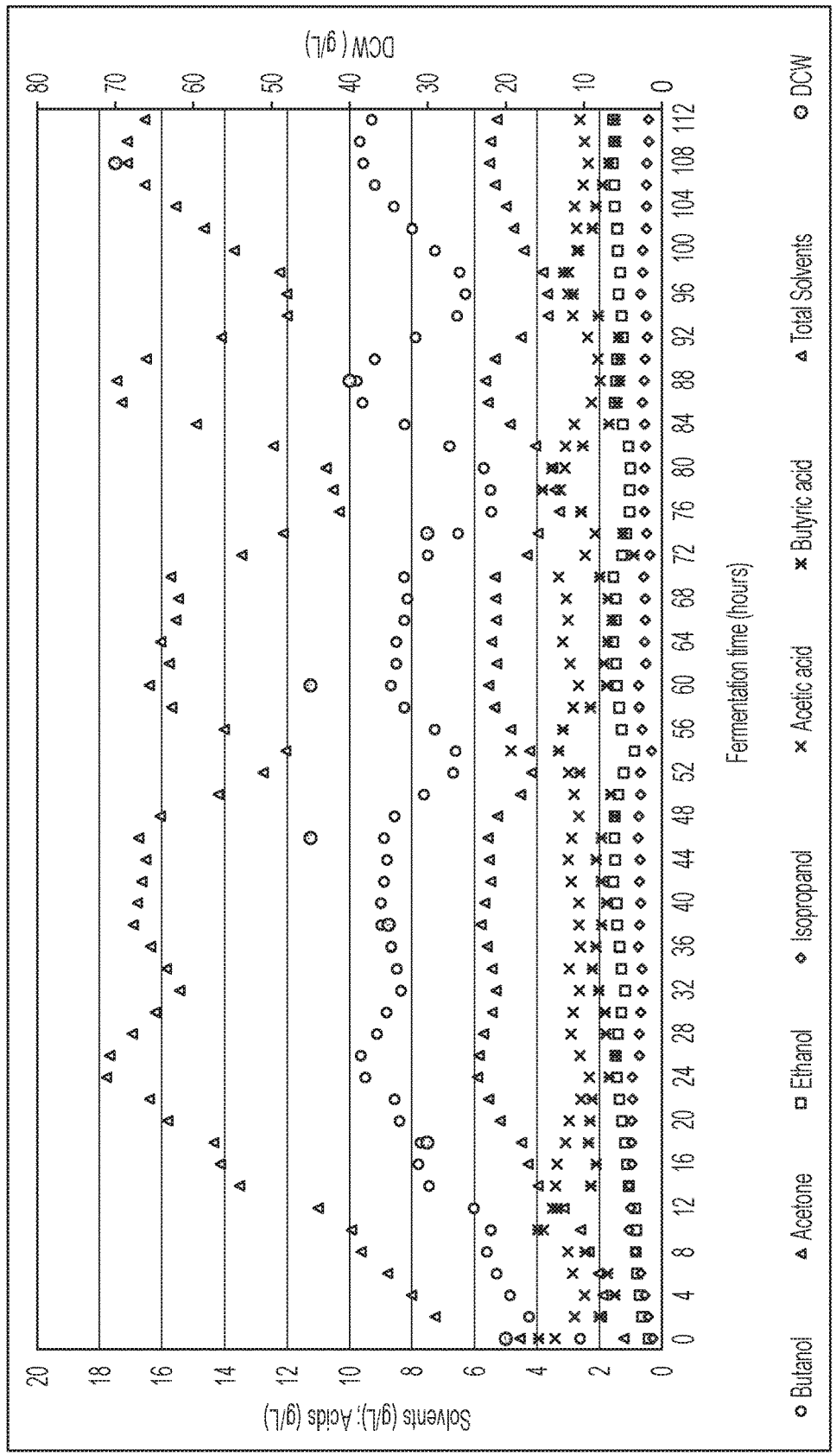
FIG. 2A is a time profile of membrane-assisted high-cell-density continuous fermentation of modified *C. acetobutylicum* ATCC 824 with pine wood $C_6$ hydrolysate, in some embodiments.
Figure 2B:
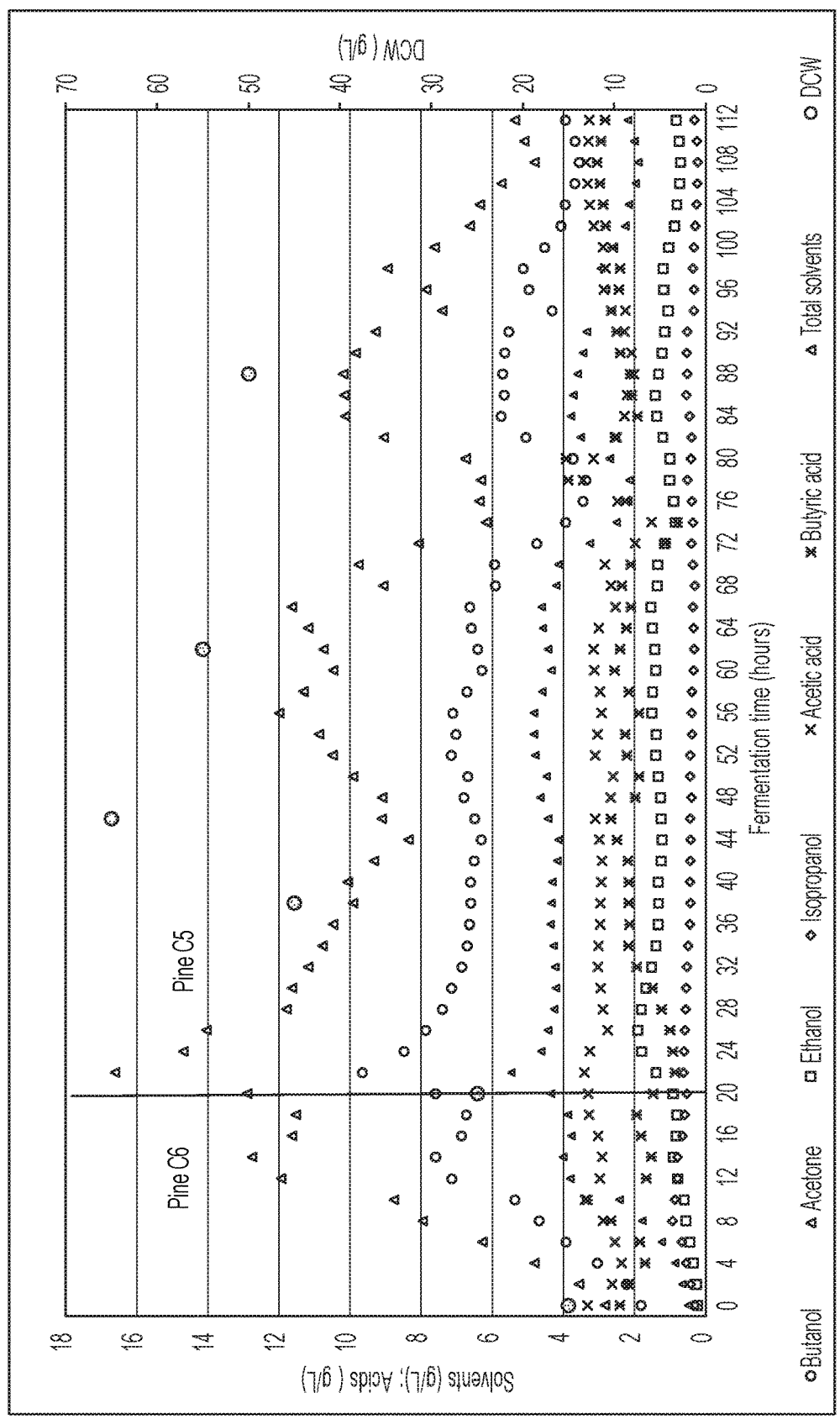
FIG. 2B is a time profile of membrane-assisted high-cell-density continuous fermentation of modified *C. acetobutylicum* ATCC 824 with pine wood $C_5$ hydrolysate, in some embodiments.
Figure 3:
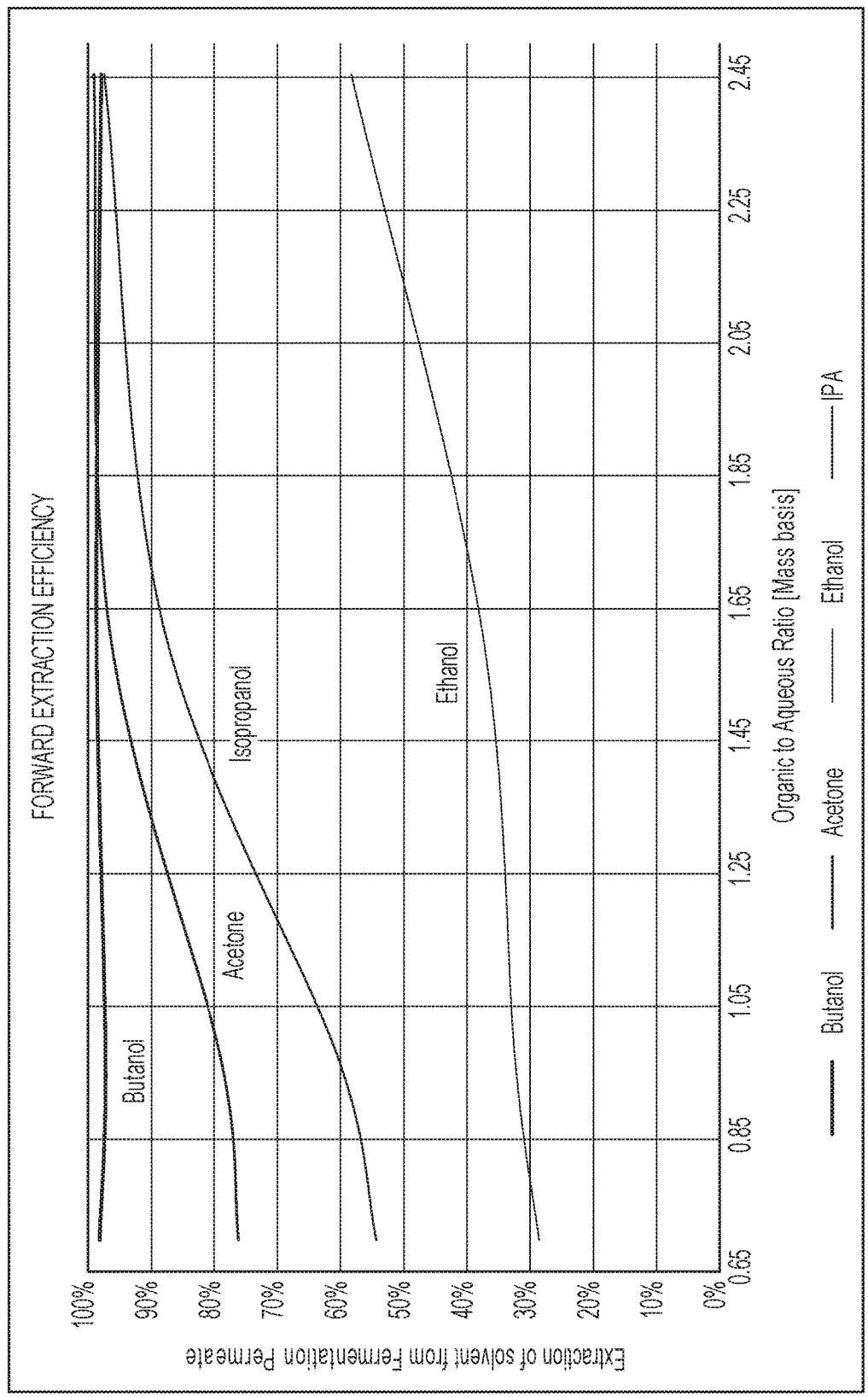
FIG. 3 is a plot of solvent extraction selectivity and efficiency during continuous liquid-liquid extraction column operation, in some embodiments.

The system of FIG. 1 has been operated by the present inventors, for production of isopropanol, n-butanol, and ethanol from pine wood-derived hydrolysates (derived from AVAP® fractionation, a type of acid-catalyzed solvent pretreatment). FIG. 2A shows a time profile of membrane-assisted high-cell-density continuous fermentation of the modified C. acetobutylicum ATCC 824 with pine wood $C_6$ hydrolysate. FIG. 2B shows a time profile of membrane-assisted high-cell-density continuous fermentation of the modified C. acetobutylicum ATCC 824 with pine wood $C_5$ hydrolysate. FIG. 3 shows a plot of solvent extraction selectivity and efficiency during continuous extraction column operation.

The intermediate return in raffinate facilitated better fermentation productivity and yield than pure xylose and water with the same cell density. Various water/raffinate ratios were used and found that there was no inhibitory effect coming from raffinate. This shows that there was no significant buildup of inhibitory components in raffinate, including the extractant itself. Another advantage of using the raffinate was extra unutilized nutrients coming back to the reactor, helping improved activity and cell growth. This helped to reduce the nutrients and growth nutrient feed to the fermentors.

Surprisingly, the hemicellulosic sugar consumption and productivity improved significantly over mixed sugar fermentations. Unexpectedly, the performance of hemicellulosic sugar fermentation improved upon introducing raffinate from the liquid-liquid extraction. Therefore, the parallel membrane-assisted fermentation using cell recycle and transfer to the hemicellulosic fermentor, along with the raffinate, provides a novel pathway to overcome the slow rate of conversion of hemicellulosic sugars and incomplete sugar utilization. The result is significantly better hemicellulosic sugar consumption compared to the current art.

In some preferred variations, a first membrane-assisted fermentation system uses highly fermentable cellulosic substrate, $C_6$-rich hydrolysate, and produces cells in excess to achieve high productivity. The excess cells are bled continuously or intermittently from the first fermentation system into the second fermentation system containing $C_5$-rich hydrolysate, where cell production is slower.

The present inventors have demonstrated an industrially relevant integrated process to produce butanol and other solvents from lignocellulosic sugars. Both hemicelluloses and celluloses from Southern Pine were fractionated into fermentable sugars using acid-catalyzed solvent pretreatment. The concentrated sugars were concurrently fermented using genetically engineered Clostridium Acetobutylicum to ethanol n-butanol, isopropanol, ethanol, and acetone in a continuous manner with solvent productivity exceeding 10 g/L/h. The solvents are recovered with a non-toxic extractant. An aqueous layer—containing unused sugars, nutrients, and metabolic intermediates—is recycled back to fermentor dilution. The total sugar yield from original biomass to final solvent is about 0.30 g/g sugars in original biomass.

This patent application discloses results from an integrated pilot-scale process from cellulosic sugars to mixed solvent products. The pilot plant was built and operated by American Process Inc. in Thomaston Biorefinery (Georgia, United States). The innovation is supported by a U.S. Department of Energy grant for Biological and Chemical Upgrading for Advanced Biofuels and Products.

A variety of lignocellulosic feedstocks have been subjected to deconstruction using AVAP® pretreatment process, where biomass is digested in sulfur dioxide-ethanol-water medium to provide monomeric sugars (see, for example, U.S. Pat. Nos. 8,030,039; 8,038,842; 8,268,125; 8,585,863; 8,864,941; 9,322,072; and 9,631,316, which are hereby incorporated by reference herein). The production plant utilizes commercial equipment scaled down to 1-3 tons of dry biomass per day. Integrated sugar processing includes process chemical recovery, enzymatic hydrolysis of cellulosic sugars, and autohydrolysis of hemicellulosic sugars. The AVAP® process conditions are benign, producing a high yield of hydrolysable sugars without significant creation of fermentation inhibitors. Sugar recovery rates over 90% have been realized.

The cellulosic and hemicellulosic sugars were conditioned for bacterial fermentation by removing residual sulfur dioxide and lignosulfonate. The residual sulfur compounds are beneficial to maintain sterility of the hydrolysate, and do not present inhibition in ethanol fermentation by yeast. However, bacteria is sensitive to sulfur compounds and conditioning must include partial removal.

Membrane-assisted fermentation with cell recycle was utilized, while the product was withdrawn continuously from the permeate. Once the desired cell density was reached, the productivity was maintained by conveying cells from the cellulosic sugar fermentor to the hemicellulosic sugar fermentor, with cells purged therefrom. An average productivity of 10 g/L/h was achieved steady-state.

Meanwhile, butanol and other solvents were extracted from the aqueous permeate using butyl butyrate as an extractant (see WO 2015193553, which is hereby incorporated by reference herein). The aqueous raffinate was recycled to fermentor dilution, returning unused sugars, nutrients, and metabolic intermediates. No negative effects were observed in the recycled raffinate. Over 90% of butanol was removed in the extractant, and distilled off. The liquid-liquid extraction was performed at near fermentor temperatures, requiring minimal thermal input. The extractant heat capacity is one-tenth of water. Organic/aqueous ratios of less than 1:1 are possible.

The pilot process was simulated using apiMAX™ biorefinery simulation tool to create an overall heat and energy balance. The process simulation shows that industrial product separation can be performed in less than half of the thermal energy consumption. The integrated process was proven to be self-sufficient in energy and provide overall yield of 0.30 g/g original biomass sugars.

In some embodiments, the process includes a selective removal of inhibitors, such as at least half of the formic acid, lignin and lignosulfonate initially present in the hydrolysate, while retaining metabolic intermediates (in particular, acetic acid) by conditioning. Conditioning may include, for example, liming for pH adjustment to 6.0 and settling, centrifugation of sludge, ultrafiltration of supernatant and centrate, and diafiltration of retentate from ultrafiltration.

Some variations provide a method of fermenting $C_5$ and $C_6$ sugars to one or more fermentation products, the method comprising:

(a) introducing a $C_6$-rich sugar feed and a first nutrient mixture to a first fermentor;

(b) introducing a $C_5$-rich sugar feed and a second nutrient mixture to a second fermentor;

(c) fermenting at least a portion of the $C_6$-rich sugar feed, in the presence of a fermentation microorganism in the first fermentor, to a first fermentation product;

(d) fermenting at least a portion of the $C_5$-rich sugar feed, in the presence of the fermentation microorganism in the second fermentor, to a second fermentation product;

(e) continuously or intermittently removing cells of the fermentation microorganism from the first fermentor, to maintain a first-fermentor microorganism cell concentration within a selected range;

(f) conveying at least a portion of the cells of the fermentation microorganism from step (e) to the second fermentor; and (g) optionally, continuously or intermittently removing cells of the fermentation microorganism from the second fermentor, to maintain a second-fermentor microorganism cell concentration within a selected range, wherein the second-fermentor microorganism cell concentration is preferably greater than the first-fermentor microorganism cell concentration.

In some embodiments, maintaining the first-fermentor microorganism cell concentration within a selected range controls foaming in the first fermentor. In these or other embodiments, maintaining the second-fermentor microorganism cell concentration within a selected range controls foaming in the second fermentor.

The method may be operated continuously, in semi-batch, or in batch.

The fermentation microorganism may be a bacteria (e.g., *Clostridium acetobutylicum* ATCC 824) or a yeast. In some embodiments, the first fermentor is operated aerobically or microaerobically. In these or other embodiments, the second fermentor is operated aerobically or microaerobically.

In certain preferred embodiments, the cells of the fermentation microorganism from the first fermentor are removed with a membrane in step (e). In these or other embodiments, the cells of the fermentation microorganism from the second fermentor are removed with a membrane in step (g).

Step (f) may include conveying fermentation broth containing nutrients from the first fermentor to the second fermentor, with or without cell separation from fermentation broth, whereby the second nutrient mixture is supplemented with additional nutrients (e.g., vitamins, minerals, metabolic intermediates, etc.). In certain embodiments, step (f) includes conveying fermentation broth containing nutrients from the first fermentor to the second fermentor, with or without cell separation from fermentation broth, wherein all of the second nutrient mixture consists of the fermentation broth containing nutrients from the first fermentor.

The first nutrient mixture may be selected to control the first-fermentor microorganism cell concentration. The second nutrient mixture may be selected to control the second-fermentor microorganism cell concentration.

In some embodiments, the selected range of the first-fermentor microorganism cell concentration is from about 10 g/L to about 75 g/L, such as from about 20 g/L to about 50 g/L (cell dry weight per liter of fermentation broth).

In some embodiments, the selected range of the second-fermentor microorganism cell concentration is from about 20 g/L to about 100 g/L, such as from about 25 g/L to about 75 g/L (cell dry weight per liter of fermentation broth). The second-fermentor microorganism cell concentration is preferably maintained or controlled to be greater than the first-fermentor microorganism cell concentration.

In certain embodiments, the second-fermentor microorganism cell concentration is about the same as, or less than, the first-fermentor microorganism cell concentration, at least for a certain period of time (e.g., transients during operation).

In certain embodiments, step (g) is not included, but the second-fermentor microorganism cell concentration stays below the first-fermentor microorganism cell concentration due to the control of the latter, and/or due to the composition of the second nutrient mixture, for example.

The first fermentation product(s) is typically the same as the second fermentation product(s). In principle, due to varying cell density and metabolic shift caused by potentially varying fermentation factors such as nutrient profile, residence time, temperature, and pH, the second fermentation product(s) may be different than the first fermentation product(s) even with the same microorganism present in both fermentors.

The first and second fermentation products may be selected from the group consisting of alcohols, organic acids, polyols, aldehydes, ketones, hydrocarbons, proteins, enzymes, and combinations thereof.

In some embodiments, the first and second fermentation products include a combination of acetone, n-butanol, and ethanol; a combination of isopropanol, n-butanol, and ethanol; or a combination of acetone, isopropanol, n-butanol, and ethanol.

The first and second fermentation products may include one or more $C_2$-$C_8$ alcohols, such as various isomers of butanol, pentanol, or hexanol.

The first and second fermentation products may include one or more acids selected from the group consisting of acetic acid, butyric acid, lactic acid, succinic acid, and combinations thereof.

The first and second fermentation products may include low-molecular-weight immiscible acids, in some embodiments.

The $C_6$-rich sugar feed may contain at least about 50%, 60%, 70%, 80%, 90%, 95%, or 99% glucose monomer on the basis of all sugars present. The $C_6$-rich sugar may further contain other $C_6$ sugars, $C_5$ sugars, and other sugars or sugar derivatives.

The $C_5$-rich sugar feed may contain less than about 50%, 40%, 30%, 20%, 10%, 5%, 3%, or 1% glucose monomer on the basis of all sugars present. The $C_5$-rich sugar typically contains significant xylose, such as at least about 50%, 60%, 70%, 80%, 90%, 95%, or 99% xylose monomer on the basis of all sugars present. The $C_5$-rich sugar may further contain other $C_5$ sugars, $C_6$ sugars, and other sugars or sugar derivatives. The $C_6$-rich sugar feed typically contains at least 80%, 90%, or 95% of the total glucose present in the combined $C_5$-rich sugar feed and $C_6$-rich sugar feed.

In some embodiments, the primary sugar is sucrose, rather than glucose. In some embodiments, the primary sugar is fructose, rather than glucose. Mixtures of glucose and fructose may also be used as the main sugars in the $C_6$-rich sugar feed.

In some embodiments, hemicellulose sugars are used as the $C_5$-rich sugar feed, regardless of the actual content of C5 sugars in the hemicellulose sugars. Depending on feedstock, hemicelluloses can contain significant quantities of $C_6$ sugars, such as mannose (especially in softwoods). Therefore, some variations of the invention provide a method of fermenting $C_6$ sugars and hemicellulose sugars to one or more fermentation products, the method comprising:

(a) introducing a $C_6$-rich sugar feed and a first nutrient mixture to a first fermentor;

(b) introducing a hemicellulose sugar feed and a second nutrient mixture to a second fermentor;

(c) fermenting at least a portion of the $C_6$-rich sugar feed, in the presence of a fermentation microorganism in the first fermentor, to a first fermentation product;

(d) fermenting at least a portion of the hemicellulose sugar feed, in the presence of the fermentation microorganism in the second fermentor, to a second fermentation product;

(e) continuously or intermittently removing cells of the fermentation microorganism from the first fermentor, to maintain a first-fermentor microorganism cell concentration within a selected range;

(f) conveying at least a portion of the cells of the fermentation microorganism from step (e) to the second fermentor; and (g) optionally, continuously or intermittently removing cells of the fermentation microorganism from the second fermentor, to maintain a second-fermentor microorganism cell concentration within a selected range, wherein the second-fermentor microorganism cell concentration is greater than the first-fermentor microorganism cell concentration.

Some variations of the invention provide a method of fermenting glucose and hemicellulose sugars to one or more fermentation products, the method comprising:

(a) introducing a glucose feed and a first nutrient mixture to a first fermentor;

(b) introducing a hemicellulose sugar feed and a second nutrient mixture to a second fermentor;

(c) fermenting at least a portion of the glucose feed, in the presence of a fermentation microorganism in the first fermentor, to a first fermentation product;

(d) fermenting at least a portion of the hemicellulose sugar feed, in the presence of the fermentation microorganism in the second fermentor, to a second fermentation product;

(e) continuously or intermittently removing cells of the fermentation microorganism from the first fermentor, to maintain a first-fermentor microorganism cell concentration within a selected range;

(f) conveying at least a portion of the cells of the fermentation microorganism from step (e) to the second fermentor; and (g) optionally, continuously or intermittently removing cells of the fermentation microorganism from the second fermentor, to maintain a second-fermentor microorganism cell concentration within a selected range, wherein the second-fermentor microorganism cell concentration is greater than the first-fermentor microorganism cell concentration.

Some variations of the invention provide a method of fermenting sucrose and hemicellulose sugars to one or more fermentation products, the method comprising:

(a) introducing a sucrose feed and a first nutrient mixture to a first fermentor;

(b) introducing a hemicellulose sugar feed and a second nutrient mixture to a second fermentor;

(c) fermenting at least a portion of the sucrose feed, in the presence of a fermentation microorganism in the first fermentor, to a first fermentation product;

(d) fermenting at least a portion of the hemicellulose sugar feed, in the presence of the fermentation microorganism in the second fermentor, to a second fermentation product;

(e) continuously or intermittently removing cells of the fermentation microorganism from the first fermentor, to maintain a first-fermentor microorganism cell concentration within a selected range;

(f) conveying at least a portion of the cells of the fermentation microorganism from step (e) to the second fermentor; and (g) optionally, continuously or intermittently removing cells of the fermentation microorganism from the second fermentor, to maintain a second-fermentor microorganism cell concentration within a selected range, wherein the second-fermentor microorganism cell concentration is greater than the first-fermentor microorganism cell concentration.

Essentially, the principles of the invention may be applied to dissimilar sugars, in which one sugar is higher quality than the other, for any reason. Some variations of the invention provide a method of fermenting two dissimilar sugars to one or more fermentation products, the method comprising:

(a) introducing a first sugar feed and a first nutrient mixture to a first fermentor;

(b) introducing a second sugar feed and a second nutrient mixture to a second fermentor;

(c) fermenting at least a portion of the first sugar feed, in the presence of a fermentation microorganism in the first fermentor, to a first fermentation product;

(d) fermenting at least a portion of the second sugar feed, in the presence of the fermentation microorganism in the second fermentor, to a second fermentation product;

(e) continuously or intermittently removing cells of the fermentation microorganism from the first fermentor, to maintain a first-fermentor microorganism cell concentration within a selected range;

(f) conveying at least a portion of the cells of the fermentation microorganism from step (e) to the second fermentor; and (g) optionally, continuously or intermittently removing cells of the fermentation microorganism from the second fermentor, to maintain a second-fermentor microorganism cell concentration within a selected range, wherein the second-fermentor microorganism cell concentration is greater than the first-fermentor microorganism cell concentration.

This disclosure provides an integrated biorefinery process, where alcohol and sulfur dioxide are used to dissolve efficiently lignin and hemicelluloses, while leaving cellulose fibers nearly intact. The cooked material is preferably washed countercurrently to remove alcohol, lignin, and dissolved hemicelluloses, while the remaining cellulose is further enzymatically saccharified to high-purity glucose sugars. These glucose sugars are cleaned of cooking chemicals and solid impurities, before fermenting with a microorganism. After filtration, the high-purity glucose sugars are comparable to dextrose sugars, which are used for fermentation with most industrial microorganisms. The sugars are converted to fermentation products via fermentation, preferably with microorganism recycle. The products are extracted into a water-immiscible extractant, and further separated by distillation. In particular, alcohol sulfite pretreatment is applied to produce cellulosic sugars, which are very low in hemicellulosic sugars. The cellulosic sugars may be detoxified and fermented with hemicellulosic sugars using suitable microorganisms, optionally using membrane-assisted recycle. The products may be separated in liquid-liquid extraction from the fermentation broth.

A first process step is pretreatment. Typical alcohol, water, and sulfur dioxide ratios by weight are between 10 and 80% of alcohol in water, and 5 to 50% of sulfur dioxide. Lignocellulosic material is cooked at a temperature from 95° C. to 170° C. for 10 minutes or more. The spent liquor consisting mainly of lignin and hemicellulosic sugars is removed from the cellulose fibers by filtration. The washed cellulose is saccharified with enzymes. Hemicelluloses are removed of cooking chemicals.

An optional process step is detoxification of the hydrolysates. This step may include neutralization, removal of solids, and catalytic oxidation of the remaining sulfur dioxide. The neutralization is preferably done with calcium oxide, magnesium oxide, ammonia or with hydrous solution thereof. The undissolved solids are filtered out to enable microorganism recycle. The catalytic oxidation may be done with hydrogen peroxide or ferrous sulfate heptahydrate as taught by Van Heiningen et al. in PCT patent publication WO2012123644, which is hereby incorporated by reference herein. The cellulosic sugars may be filtered from insolubles and evaporated to a syrup. The cellulosic sugars containing mostly glucose may be fermented separately from hemicellulosic sugars, if the fermentation organism prefers a single sugar over a mixture.

Another process step is fermentation with a membrane-assisted recycle of the microorganisms, wherein sugars are converted to products, as described in detail above. The products may include n-butanol from genetically modified yeast, or a mixture of acetone, n-butanol and ethanol from Clostridia family bacteria, or a mixture of isopropanol, n-butanol and ethanol from Clostridia bacteria. In some embodiments, a genetically modified *Clostridium* may include an isopropanol gene that has been cloned by transferring adh gene (which catalyzes the reduction of acetone to isopropanol) from another organism, which may be a different *Clostridium* or an *E-coli*, for example.

Other potential fermentation products include isomers of propanol, butanol, and pentanol, and/or organic aliphatic acids from naturally occurring and genetically modified organisms. Hemicellulosic sugars may be added to increase production or fermented separately. In various embodiments, the fermentation product is selected from $C_2$-$C_{12}$ linear or branched alcohols, $C_2$-$C_{12}$ linear or branched acids, $C_2$-$C_{12}$ linear or branched hydrocarbons, or isomers, derivatives, or reaction products thereof, or combinations of any of the foregoing.

The fermentation products are preferably passed through a membrane, wherein the microorganism will be recycled back to the fermentor and the products sent to downstream purification. The membrane recycle system preferably is configured to remove microorganisms to control cell density in the fermentor. Additionally, fresh microorganisms may be propagated into the fermentor along with nutrition supply.

The fourth process step is extraction of the solvents. A liquid-liquid extraction is used to concentrate dilute fermentation products to reduce energy requirements, as compared to the traditional distillation methods. Energy integration and heat recovery, using one or more principles described in detail hereinbelow, further reduce the energy consumption—making recovery more efficient than traditional ethanol distillation at high broth concentration. Thus, the process can be self-sufficient in thermal and electrical consumption by combusting biomass lignin and the process residues. The extractant is a water-immiscible solvent, such as methyl ethyl ketone, methyl isobutyl ketone, dodecanol, or mixture of extractants such as decanol in oleyl alcohol. The preferred extractant one or more aldol acids such as propionic, butyric, levulinic, or succinic acid, or butyl butyrate.

The fifth process step is purification, wherein solutes are separated from extractant by distillation. The distillation is performed with indirect steam to remove more volatile solutes from the extractant. If necessary, the solutes are separated and purified in fractional distillation columns.

This step may also be practiced separately from the hemicellulosic product distillation. Optionally, distillation is practiced at low temperature, enabling part of the distillation bottoms containing yeast and enzymes to be recycled back to the enzymatic hydrolysis step.

The alcohol purification step may be combined with the extraction step to improve heat recovery. The bottoms of the fermentation may be sent to the evaporator to recover unfermentable solids for energy generation or other uses.

In some variations, the invention provides a process for fractionating lignocellulosic biomass into cellulose, hemicellulose, and lignin, the process comprising:

(a) in a digestor, fractionating a feedstock comprising lignocellulosic biomass in the presence of a solvent for lignin, sulfur dioxide, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) saccharifying at least some of the cellulose-rich solids to produce glucose;

(e) recovering the hemicellulosic monomers and the glucose, separately or in a combined stream, as fermentable sugars;

(f) fermenting at least a portion of the fermentable sugars to a fermentation product having a higher normal boiling point than water, or being immiscible with water, or both of these; and (g) recovering the fermentation product, wherein the process preferably includes process integration of mass and/or energy between at least two of steps (a)-(g).

In preferred embodiments, the process integration includes pinch analysis and energy optimization one or more steps, preferably all steps, in the process.

In some embodiments, the process integration includes concentrating the fermentable sugars, recovering a condensate stream therefrom, and introducing the condensate stream to a fermentor feed stream and/or to a fermentor nutrient system.

In some embodiments, the process integration includes concentrating the fermentable sugars, recovering a condensate stream therefrom, and using the condensate stream for washing the cellulose-rich solids in step (b).

In some embodiments, the process integration includes sterilizing a fermentor or fermentor feed stream with a vapor take-off from one or more evaporators used for concentrating the fermentable sugars and/or one or more evaporators used for concentrating the fermentation product.

In some embodiments, the process integration includes pre-cooling a fermentor feed stream with a product stream comprising the fermentation product.

In some embodiments, the process integration includes concentrating the fermentation product in a non-externally-heated effect of a multiple-effect evaporation unit, such as the last effect of the multiple-effect evaporation unit.

In some embodiments, the process integration includes using vapor recompression and vacuum pumping to concentrate the fermentation product, to minimize cooling water requirements.

In some embodiments, the process integration includes concentrating one or more organic waste streams and combusting the one or more organic waste streams with lignin or another biomass-derived material.

In some embodiments, the process integration includes recovering the solvent for lignin that remains absorbed in cellulose-rich solids after step (b), by feeding one or more condensate streams and/or one or more waste streams to a stripping column.

In some embodiments, the process integration includes utilizing a rectifier reflux condensor to pre-evaporate stillage from a fermentation product distillation column. The process integration may also include preheating diminerlaized water or preheating turbine condenser condensate, for example.

In some embodiments, the process integration includes integration of an evaporator associated with step (d), with a sulfur dioxide stripper and a beer column stillage evaporator.

The biomass feedstock may be selected from hardwoods, softwoods, forest residues, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.).

Various moisture levels may be associated with the starting biomass. The biomass feedstock need not be, but may be, relatively dry. In general, the biomass is in the form of a particulate or chip, but particle size is not critical in this invention.

The solvent for lignin preferably facilitates a higher mass transfer rate of the sulfur dioxide into the lignocellulosic biomass, compared to the mass transfer rate of sulfur dioxide into the lignocellulosic biomass with water alone. For example, ethanol facilitates better $SO_2$ mass transfer because ethanol (with dissolved $SO_2$) is able to penetrate into biomass pores more efficiently than water.

In some embodiments, the solvent for lignin comprises an oxygenated hydrocarbon, such as an aliphatic alcohol which may be a $C_1$-$C_8$ alcohol, for example, or an aromatic alcohol, such as phenol. In some embodiments, the solvent for lignin comprises an aliphatic or aromatic hydrocarbon.

In some embodiments, the solvent for lignin comprises an organic acid. For example, without limitation, the organic acid may be selected from the group consisting of acetic acid, formic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, and combinations thereof.

In these or other embodiments, the solvent for lignin comprises an inorganic acid, such as concentrated phosphoric acid. In certain embodiments, the solvent for lignin comprises an ionic liquid.

The process may further include recovering the lignin, lignosulfonates, or both of these. Recovery of lignin typically involves removal of solvent, dilution with water, adjustment of temperature or pH, addition of an acid or base, or some combination thereof.

The sulfur dioxide may be present in a liquid-phase concentration of about 1 wt % to about 50 wt % during step (a), or about 6 wt % to about 30 wt %, or about 9 wt % to about 20 wt %, in various embodiments.

Step (b) typically includes washing of the cellulose-rich solids, which preferably includes countercurrent washing of the cellulose-rich solids.

Hydrolyzing the hemicellulose contained in the liquor, in step (c), may be catalyzed by lignosulfonic acids that are generated during step (a).

The fermentation product may include an organic acid, such as (but not limited to) organic acids selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof. In certain embodiments, the organic acid is succinic acid. "Derivatives" may be salts of these acids, or esters, or reaction products to convert the acid to another molecule that is not an acid. For example, when the fermentation product is succinic acid, it may be further converted to 1,4-butanediol as a derivative using known hydrotreating chemistry.

The fermentation product may include an oxygenated compound, such as (but not limited to) oxygenated compounds selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

In some embodiments, the oxygenated compound is a $C_3$ or higher alcohol or diol, such as 1-butanol, isobutanol, 1,4-butanediol, 2,3-butanediol, or mixtures thereof.

The fermentation product may include a hydrocarbon, such as isoprene, farnasene, and related compounds.

Multiple fermentation products may be produced in a single fermentor, in co-product production or as a result of byproducts due to contaminant microorganisms. For example, during fermentation to produce lactic acid, ethanol is a common byproduct due to contamination (and vice-versa).

Multiple fermentation products may be produced in separate fermentors. In some embodiments, a first fermentation product, such as an organic acid, is produced from glucose (hydrolyzed cellulose) while a second fermentation product, such as ethanol, is produced from hemicellulose sugars. Or, in some embodiments, different fermentations are directed to portions of feedstock having varying particle size, crystallinity, sugar quality, or other properties.

In some embodiments, different fermentations are directed to portions of whole biomass that is separated into a starch or sucrose-rich fraction, and a cellulose-rich fraction (for example, corn starch/stover or sugarcane syrup/bagasse). For example, from raw corn, an organic acid or polyol may be produced from starch (hydrolyzed to glucose), the same or a different organic acid or polyol may be produced from cellulose (hydrolyzed to glucose), and ethanol may be produced from hemicellulose sugars. Many variations are possible, as will be recognized by a person skilled in the biorefinery art, in view of the present disclosure.

The solvent for lignin may include a component that is the same as the fermentation product. In some embodiments, the solvent for lignin is the same compound as the fermentation product. For example, the solvent and the fermentation product may be 1-butanol, or lactic acid, succinic acid, or 1,4-butanediol. Of course, other solvents may be present even when these products are utilized as solvents or co-solvents. Beneficially, a portion of the fermentation product may be recycled to step (a) for use as the solvent for lignin.

In some embodiments, the fermentation product includes an enzymatically isomerized variant of at least a portion of the fermentable sugars. For example, the enzymatically isomerized variant may include fructose which is isomerized from glucose. In some embodiments, glucose, which is normally D-glucose, is isomerized with enzymes to produce L-glucose.

In some embodiments, the fermentation product includes one or more proteins, amino acids, enzymes, or microorganisms. Such fermentation products may be recovered and used within the process; for example, cellulase or hemicellulase enzymes may be used for hydrolyzing cellulose-rich solids or hemicellulose oligomers.

In some embodiments, the hydrolysis catalyst is present in a liquid-phase concentration of about 1 wt % to about 50 wt % during step (a), such as about 6 wt % to about 30 wt %, or about 9 wt % to about 20 wt %. The hydrolysis catalyst in step (a) may be selected from the group consisting of sulfur dioxide, sulfur trioxide, sulfurous acid, sulfuric acid, sulfonic acid, lignosulfonic acid, elemental sulfur, polysulfides, and combinations or derivatives thereof.

In some embodiments, the hydrolyzing in step (c) utilizes the hydrolysis catalyst from step (a), or a reaction product thereof. For example, in certain embodiments the hydrolysis catalyst is sulfur dioxide and the reaction product is lignosulfonic acid. In other embodiments, the hydrolyzing in step (c) utilizes hemicellulase enzymes as hydrolysis catalyst.

In some embodiments, the solvent for lignin also contains the functionality of a hydrolysis catalyst, i.e. there is not a separate hydrolysis catalyst present. In particular, when the solvent for lignin is an organic acid, it may also function as the hydrolysis catalyst.

In some embodiments, the process further comprises saccharifying at least some of the cellulose-rich solids to produce glucose. In these or other embodiments, the process further comprises recovering or further treating or reacting at least some of the cellulose-rich solids as a pulp precursor or product. When glucose is produced (by acid or enzyme hydrolysis of the cellulose), that glucose may form part of the fermentable sugars, either separately from the hemicellulose-derived fermentable sugars, or as a combined sugar stream.

In some embodiments, the fermentation product is ethanol, 1-butanol, succinic acid, 1,4-butanediol, or a combination thereof. In some embodiments, the solvent for lignin includes a component that is the same as the fermentation product, or is the same compound as the fermentation product. Thus a portion of the fermentation product may be recycled to step (a) for use as the solvent for lignin.

Some variations provide a process for fractionating lignocellulosic biomass into cellulose, hemicellulose, and lignin, the process comprising:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) recovering the hemicellulosic monomers as fermentable sugars;

(e) fermenting at least a portion of the fermentable sugars to a fermentation product having a relative volatility with water of less than 1.0, and/or being water-immiscible; and (f) recovering the fermentation product, wherein the process preferably includes process integration of mass and/or energy between at least two of steps (a)-(f).

The relative volatility of the fermentation product with water may be calculated at any relevant temperature, such as 25° C. (i.e. ambient conditions), or at the temperature of the digestor in step (a), or at the temperature of recovering (e.g., distillation) in step (f). It should also be noted that the relative volatility of the fermentation product with water technically depends on the other components present in solution, due to multicomponent thermodynamic equilibria. It is possible that the ideal relative volatility of a product with water is greater (or less) than 1.0 at a given temperature, but that in actual solution, the relative volatility of the product with water is less (or greater) than 1.0.

In any of the embodiments described above, the process may further include hydrolyzing at least a portion of the cellulose-rich solids into glucose, and optionally fermenting the glucose to the fermentation product.

Some variations provide a process for fractionating lignocellulosic biomass into cellulose, hemicellulose, and lignin, the process comprising:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) hydrolyzing the hemicellulose contained in the liquor to produce hemicellulosic monomers;

(c) substantially separating the cellulose-rich solids from the liquor;

(d) recovering the hemicellulosic monomers as fermentable sugars;

(e) fermenting at least a portion of the fermentable sugars to a fermentation product having a relative volatility with water of less than 1.0 and/or being water-immiscible; and (f) recovering the fermentation product, wherein the process preferably includes process integration of mass and/or energy between at least two of steps (a)-(f), and wherein steps (a) and (b) are optionally combined in a single vessel.

Some variations provide a process for fractionating lignocellulosic biomass into cellulose, hemicellulose, and lignin, the process comprising:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) hydrolyzing the cellulose-rich solids to produce glucose;

(c) hydrolyzing the hemicellulose contained in the liquor to produce hemicellulosic monomers;

(d) recovering the glucose and the hemicellulosic monomers as fermentable sugars, separately or in a combined stream;

(e) fermenting at least a portion of the fermentable sugars to a fermentation product having a relative volatility with water of less than 1.0, and/or being water-immiscible; and (f) recovering the fermentation product, wherein the process preferably includes process integration of mass and/or energy between at least two of steps (a)-(f).

Reaction conditions and operation sequences may vary widely. Some embodiments employ conditions described in U.S. Pat. No. 8,030,039, issued Oct. 4, 2011; U.S. Pat. No. 8,038,842, issued Oct. 11, 2011; or U.S. Pat. No. 8,268,125, issued Sep. 18, 2012. Each of these commonly owned patents is hereby incorporated by reference herein in its entirety. In some embodiments, the process is a variation of the AVAP® process technology which is commonly owned with the assignee of this patent application.

In some embodiments, a first process step is "cooking" (equivalently, "digesting") which fractionates the three lignocellulosic material components (cellulose, hemicellulose, and lignin) to allow easy downstream removal. Specifically, hemicelluloses are dissolved and over 50% are completely hydrolyzed; cellulose is separated but remains resistant to hydrolysis; and part of the lignin is sulfonated into water-soluble lignosulfonates.

The lignocellulosic material is processed in a solution (cooking liquor) of aliphatic alcohol, water, and sulfur dioxide. The cooking liquor preferably contains at least 10 wt %, such as at least 20 wt %, 30 wt %, 40 wt %, or 50 wt % of a solvent for lignin. For example, the cooking liquor may contain about 30-70 wt % solvent, such as about 50 wt % solvent. The solvent for lignin may be an aliphatic alcohol, such as methanol, ethanol, 1-propanol, 2-propanol, 1-butanol, 2-butanol, isobutanol, 1-pentanol, 1-hexanol, or cyclohexanol. The solvent for lignin may be an aromatic alcohol, such as phenol or cresol. Other lignin solvents are possible, such as (but not limited to) glycerol, methyl ethyl ketone, or diethyl ether. Combinations of more than one solvent may be employed.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The cooking liquor preferably contains sulfur dioxide and/or sulfurous acid ($H_2SO_3$). The cooking liquor preferably contains $SO_2$, in dissolved or reacted form, in a concentration of at least 3 wt %, preferably at least 6 wt %, more preferably at least 8 wt %, such as about 9 wt %, 10 wt %, 11 wt %, 12 wt %, 13 wt %, 14 wt %, 15 wt %, 20 wt %, 25 wt %, 30 wt % or higher. The cooking liquor may also contain one or more species, separately from $SO_2$, to adjust the pH. The pH of the cooking liquor is typically about 4 or less.

Sulfur dioxide is a preferred acid catalyst, because it can be recovered easily from solution after hydrolysis. The majority of the $SO_2$ from the hydrolysate may be stripped and recycled back to the reactor. Recovery and recycling translates to less lime required compared to neutralization of comparable sulfuric acid, less solids to dispose of, and less separation equipment. The increased efficiency owing to the inherent properties of sulfur dioxide mean that less total acid or other catalysts may be required. This has cost advantages, since sulfuric acid can be expensive. Additionally, and quite significantly, less acid usage also will translate into lower costs for a base (e.g., lime) to increase the pH following hydrolysis, for downstream operations. Furthermore, less acid and less base will also mean substantially less generation of waste salts (e.g., gypsum) that may otherwise require disposal.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 65° C. to 175° C., for example 75° C., 85° C., 95° C., 105° C., 115° C., 125° C., 130° C., 135° C., 140° C., 145° C., 150° C., 155° C., 165° C. or 170° C., and corresponding pressures from about 1 atmosphere to about 15 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with ethanol and sulfur dioxide vapor in equilibrium with moisture. The cooked biomass is washed in alcohol-rich solution to recover lignin and dissolved hemicelluloses, while the remaining pulp is further processed. In some embodiments, the process of fractionating lignocellulosic material comprises vapor-phase cooking of lignocellulosic material with aliphatic alcohol (or other solvent for lignin), water, and sulfur dioxide. See, for example, U.S. Pat. Nos. 8,038,842 and 8,268,125 which are incorporated by reference herein.

A portion or all of the sulfur dioxide may be present as sulfurous acid in the extract liquor. In certain embodiments, sulfur dioxide is generated in situ by introducing sulfurous acid, sulfite ions, bisulfite ions, combinations thereof, or a salt of any of the foregoing. Excess sulfur dioxide, following hydrolysis, may be recovered and reused.

In some embodiments, sulfur dioxide is saturated in water (or aqueous solution, optionally with an alcohol) at a first temperature, and the hydrolysis is then carried out at a second, generally higher, temperature. In some embodiments, sulfur dioxide is sub-saturated. In some embodiments, sulfur dioxide is super-saturated. In some embodiments, sulfur dioxide concentration is selected to achieve a certain degree of lignin sulfonation, such as 1%, 2%, 3%, 4%, 5%, 6%, 7%, 8%, 9%, or 10% sulfur content. $SO_2$ reacts chemically with lignin to form stable lignosulfonic acids which may be present both in the solid and liquid phases.

The concentration of sulfur dioxide, additives, and aliphatic alcohol (or other solvent) in the solution and the time of cook may be varied to control the yield of cellulose and hemicellulose in the pulp. The concentration of sulfur dioxide and the time of cook may be varied to control the yield of lignin versus lignosulfonates in the hydrolysate. In some embodiments, the concentration of sulfur dioxide, temperature, and the time of cook may be varied to control the yield of fermentable sugars.

Once the desired amount of fractionation of both hemicellulose and lignin from the solid phase is achieved, the liquid and solid phases are separated. Conditions for the separation may be selected to minimize the reprecipitation of the extracted lignin on the solid phase. This is favored by conducting separation or washing at a temperature of at least the glass-transition temperature of lignin (about 120° C.).

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digestor, for example. The flash vapor from the pressure reduction may be collected into a cooking liquor make-up vessel. The flash vapor contains substantially all the unreacted sulfur dioxide which may be directly dissolved into new cooking liquor. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent and sulfur dioxide. The solution may or may not contain residual solvent (e.g. alcohol). In some embodiments, sulfur dioxide is added or allowed to pass through to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In some embodiments, no additional acid is introduced, but lignosulfonic acids produced during the initial cooking are effective to catalyze hydrolysis of hemicellulose oligomers to monomers. In various embodiments, this step utilizes sulfur dioxide, sulfurous acid, sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove and recover sulfur dioxide and alcohol, and for removal of potential fermentation-inhibiting side products. The evaporation process may be under vacuum or pressure, from about −0.1 atmospheres to about 10 atmospheres, such as about 0.1 atm, 0.3 atm, 0.5 atm, 1.0 atm, 1.5 atm, 2 atm, 4 atm, 6 atm, or 8 atm.

Recovering and recycling the sulfur dioxide may utilize separations such as, but not limited to, vapor-liquid disengagement (e.g. flashing), steam stripping, extraction, or combinations or multiple stages thereof. Various recycle ratios may be practiced, such as about 0.1, 0.2, 0.3, 0.4, 0.5, 0.6, 0.7, 0.8, 0.9, 0.95, or more. In some embodiments, about 90-99% of initially charged $SO_2$ is readily recovered by distillation from the liquid phase, with the remaining 1-10% (e.g., about 3-5%) of the $SO_2$ primarily bound to dissolved lignin in the form of lignosulfonates.

In a preferred embodiment, the evaporation step utilizes an integrated alcohol stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

When the fermentation will employ bacteria, such as Clostridia bacteria, it is preferable to further process and condition the hydrolysate to raise pH and remove residual $SO_2$ and other fermentation inhibitors. The residual $SO_2$ (i.e., following removal of most of it by stripping) may be catalytically oxidized to convert residual sulfite ions to sulfate ions by oxidation. This oxidation may be accomplished by adding an oxidation catalyst, such as $FeSO4.7H_2O$, that oxidizes sulfite ions to sulfate ions. Preferably, the residual $SO_2$ is reduced to less than about 100 ppm, 50 ppm, 25 ppm, 10 ppm, 5 ppm, or 1 ppm.

In some embodiments, the process further comprises recovering the lignin as a co-product. The sulfonated lignin may also be recovered as a co-product. In certain embodiments, the process further comprises combusting or gasifying the sulfonated lignin, recovering sulfur contained in the sulfonated lignin in a gas stream comprising reclaimed sulfur dioxide, and then recycling the reclaimed sulfur dioxide for reuse.

The process lignin separation step is for the separation of lignin from the hydrolysate and can be located before or after the final reaction step and evaporation. If located after, then lignin will precipitate from the hydrolysate since alcohol has been removed in the evaporation step. The remaining water-soluble lignosulfonates may be precipitated by converting the hydrolysate to an alkaline condition (pH higher than 7) using, for example, an alkaline earth oxide, preferably calcium oxide (lime). The combined lignin and lignosulfonate precipitate may be filtered. The lignin and lignosulfonate filter cake may be dried as a co-product or burned or gasified for energy production. The hydrolysate from filtering may be recovered and sold as a concentrated sugar solution product or further processed in a subsequent fermentation or other reaction step.

Native (non-sulfonated) lignin is hydrophobic, while lignosulfonates are hydrophilic. Hydrophilic lignosulfonates may have less propensity to clump, agglomerate, and stick to surfaces. Even lignosulfonates that do undergo some condensation and increase of molecular weight, will still have an $HSO_3$ group that will contribute some solubility (hydrophilic).

In some embodiments, the soluble lignin precipitates from the hydrolysate after solvent has been removed in the evaporation step. In some embodiments, reactive lignosulfonates are selectively precipitated from hydrolysate using excess lime (or other base, such as ammonia) in the presence of aliphatic alcohol. In some embodiments, hydrated lime is used to precipitate lignosulfonates. In some embodiments, part of the lignin is precipitated in reactive form and the remaining lignin is sulfonated in water-soluble form.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

The cellulose-rich material is highly reactive in the presence of industrial cellulase enzymes that efficiently break the cellulose down to glucose monomers. It has been found experimentally that the cellulose-rich material, which generally speaking is highly delignified, rapidly hydrolyzes to glucose with relatively low quantities of enzymes. For example, the cellulose-rich solids may be converted to glucose with at least 80% yield within 24 hours at 50° C. and 2 wt % solids, in the presence of a cellulase enzyme mixture in an amount of no more than 15 filter paper units (FPU) per g of the solids. In some embodiments, this same conversion requires no more than 5 FPU per g of the solids.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

In some embodiments, the cellulose-rich material is further processed into one more cellulose products. Cellulose products include market pulp, dissolving pulp (also known as α-cellulose), fluff pulp, purified cellulose, paper, paper products, and so on. Further processing may include bleaching, if desired. Further processing may include modification of fiber length or particle size, such as when producing nanocellulose or nanofibrillated or microfibrillated cellulose. It is believed that the cellulose produced by this process is highly amenable to derivatization chemistry for cellulose derivatives and cellulose-based materials such as polymers.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives. The sulfonated lignin may be sold as a lignosulfonate product, or burned for fuel value.

The present invention also provides systems configured for carrying out the disclosed processes, and compositions produced therefrom. Any stream generated by the disclosed processes may be partially or completed recovered, purified or further treated, and/or marketed or sold.

Apparatus may be configured to carry out the processes disclosed. In some embodiments, a system may be assembled for fractionating lignocellulosic biomass into cellulose, hemicellulose, and lignin, the system comprising elements configured to optionally (i.e., when the system is operating) perform the steps of:

(a) in a digestor, fractionating a feedstock comprising lignocellulosic biomass feedstock in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce hemicellulosic monomers;

(d) recovering the hemicellulosic monomers as fermentable sugars;

(e) fermenting at least a portion of the fermentable sugars to a fermentation product; and (f) recovering the fermentation product.

The present invention also provides one or more products, coproducts, and byproducts produced by a process as described. In preferred embodiments, a product comprises the fermentation product or a derivative thereof. In addition, an intermediate may be produced within a process, and recovered. For example, the intermediate may include purified fermentable sugars in dried form, crystallized form, pressed form, or slurried form.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

EXAMPLES

Example 1

Sugar cane straw was converted to sugars using sulfur dioxide-ethanol-water fractionation followed by enzymatic hydrolysis of the cellulosic fraction. The $C_5$-rich sugars were hydrolyzed by heating at 120° C. Both streams were further subjected to overliming using 15% CaO suspension to pH 10.5 and catalytic oxidation using FeSO4.7$H_2$O at 60° C. with agitation and aeration.

The $C_6$-rich stream was fermented in two concentrations, 53 g/L (fermentation A) and 65 g/L (fermentation B). The $C_5$-rich stream at a weight ratio 10:90 was added to the $C_6$-rich stream in the last fermentation (fermentation C). Fermentations were performed in batch mode using modified bacteria *Clostridium acetobutylicum* ATCC 824. The pH of the conditioned sugar streams was adjusted to 6.8 using 72% sulfuric acid. Other medium components were supplemented as follows: magnesium sulfate 0.2 g/L, sodium chloride 0.01 g/L, manganese sulfate 0.01 g/L, iron sulfate 0.01 g/L, potassium dihydrogen phosphate 0.5 g/L, di-potassium hydrogen phosphate 0.5 g/L, ammonium acetate 2.2 g/L, thiamin 0.1 g/L, p-aminobenzoic acid 0.1 g/L, calcium carbonate 3 g/L, and soy meal 5 g/L. Regarding the soy meal, refer to U.S. Provisional Patent App. No. 62/426,639 for "IMPROVED SOLVENT PRODUCTION USING *CLOSTRIDIUM* BY SUPPLEMENTING SOY COMPOUNDS," filed Nov. 28, 2016, which is hereby incorporated by reference herein.

The modified *Clostridium acetobutylicum* ATCC 824 strain was propagated for 24-28 h in Reinforced Clostridia Medium (RCM) after spore activation by heat shock treatment (80° C. for 10 minutes). The fermentors were inoculated when the OD at 600 nm was 0.5-0.6 with 10-fold dilution in a propagation bottle. The working volume in the fermentor was 1 L and the inoculation was 5% v/v. The fermentation was carried out at 37° C. and pH 5. During fermentation, the pH was allowed to drop to 5 and maintained using aqueous ammonia.

Table 1 shows the results of the batch fermentations.

TABLE 1

Results of Batch Fermentations in Example 1.

| Fermentation | | A | B | C |
|---|---|---|---|---|
| Initial Sugars (g/L) | Total | 53 | 65 | 62 |
| | Glucose | 46 | 56 | 50 |
| | Xylose | 6 | 8 | 11 |
| Final time, hr | | 92 | 92 | 96 |
| Total Solvents (g/L) | | 15.7 | 18.6 | 17.7 |
| Yield on sugars (g/g) | | 0.29 | 0.29 | 0.28 |
| Sugar Utilization % | Total | 96 | 91 | 83 |
| | Glucose (%) | 100 | 100 | 100 |
| | Xylose (%) | 80 | 40 | 26 |

The xylose utilization in the $C_6$-rich hydrolysate in fermentation A was 80%, but reduced in half to 40% by increasing the concentration of initial feed in fermentation B. By introducing additional xylose in the $C_5$ stream, the xylose utilization further reduced to 26%. Therefore, the glucose utilization is favored in mixed sugar fermentations.

Example 2

Corn Stover was fractionated using sulfur dioxide-ethanol-water pretreatment and the cellulose fraction was enzymatically hydrolyzed to contain 66.9 g/L of glucose and 3.6 g/L xylose. The same conditioning as in Example 1 was performed. Nutrients were added (also as in Example 1) to reach sugar concentrations between 50 and 60 g/L. Modified *C. acetobutylicum* ATCC 824 spores were germinated in Reinforced Clostridial Medium (RCM) by treating them with a heat shock at 80° C. for 10 minutes, followed by cooling on ice for one minute. Subsequently, the culture was grown for 24 hours at 37° C. in anaerobic conditions. When the OD at 600 nm reached 4-5, the culture was inoculated to medium: $CH_3COONH_4$ 2.2 g/L, $KH_2PO_4$ 0.5 g/L, $K_2HPO_4$ 0.5 g/L, $MnSO_4.7H_2O$ 0.01 g/L, NaCl 0.01 g/L, $MgSO_4$ 0.20 g/L, $FeSO_4.7H_2O$ 0.01 g/L, thiamine HCl 0.1 g/L, casein hydrolysate 5 g/L, and p-aminobenzoic acid 0.1 g/L.

The initial batch culture was cultivated for 24 hours, after which the broth in the bioreactor was recirculated through the membrane module by a pump. The permeate from the module was collected, and the broth was concentrated 10-fold. After concentration, continuous culture was initiated by the feeding medium with cell recycling. The total cell concentration was determined in terms of dry cell weight (DCW). The pH in the reactor was maintained at 5.1 using aqueous ammonia.

The DCW increased with time reaching a maximum DCW of 22.2 g/L, compared to 2-3 g/L in normal batch fermentation. The maximum total solvent productivity observed was 2.33 g/L/h and solvent yield 0.29 g/g of sugars consumed.

Example 3

Corn stover was fractionated to generate a $C_6$-rich hydrolysate as in Example 1, with an average composition of 56 g/L glucose and 6 g/L of hemicellulosic sugars, mainly xylose, in the $C_6$-rich hydrolysate. The propagation and media preparation and fermentation was performed as described in Example 2. The cell density was controlled to around 30 g/L DCW. The pH in the reactor was maintained with dilute aqueous ammonia at 4.8. The average total solvents over the period of 200 h were 13.24 g/L, with productivity of 8.5 g/L/h and yield 0.29 g/g sugar.

The cells bled from the $C_6$ fermentor were introduced to the $C_5$ fermentor as shown in FIG. 1. The $C_5$ fermentor was continuously fed with hydrolyzed corn stover $C_5$-rich hydrolyzate containing 6 g/L glucose and 38 g/L xylose. The average total solvent productivity observed for the total run period of 200 h was 3.9 g/L/h. The average total solvent productivity observed for 72 h with the desired cell density was 6.3 g/L/h and yield 0.32 g/g on consumed monosaccharide. The glucose utilization was 100% and xylose utilization was 66% of the sugars fed to the $C_5$ fermentor. The conversion rates of xylose and arabinose were improved by introducing concentrate from the $C_6$ fermentor. Therefore, high cell density allowed converting xylose efficiently along with residual sugars and other intermediate products.

Example 4

Cellulosic and hemicellulosic hydrolysates were obtained from pine using sulfur dioxide-ethanol-water pretreatment. The concentrated cellulose enzymatic hydrolysate after clarification contained (in g/L) glucose 622.57, xylose 26.48, galactose 4.9, arabinose 2.13, mannose 12.84, and acetic acid 0.04.

The hemicellulosic hydrolysate was conditioned using overliming with 20% (w/w) lime to pH 10.0, and then adjusted back to pH 6.0 with 75% phosphoric acid. The supernatant from clarified hydrolysate was processed by a membrane filtration of 4,000 molecular weight cut-off (MWCO). The concentrated permeate was treated with activated carbon and subjected to ion exchange (IX) with cationic and anionic resins. An overall 37% loss of original sugars was determined. The hemicellulosic hydrolysate after conditioning steps contained (in g/L): glucose 12.82, xylose 33.85, galactose 14.62, arabinose 4.66, mannose 35.20, acetic acid 0.54, levulinic acid 0.15, and hydroxymethylfurfural (HMF) 0.04.

The nutrient stocks and hydrolysates were sterilized by autoclaving at 121° C. for 30 minutes. The modified strain of Clostridium acetobutylicum ATCC 824 (DSM 792) with integrated ADH gene was used for the fermentation. Spores (2.5% v/v) were germinated, and the culture was grown for 24 h at 37° C. in anaerobic conditions. When the OD at 600 nm reached 4-5, the culture was inoculated to batch propagation medium. The grown culture was inoculated to batch propagation medium at 5% v/v. Pine cellulosic hydrolysate was used as a carbon source and pH was controlled at 5.1.

The batch cultivation was conducted for 22 h, after which the broth was gradually recirculated through the membrane module and concentrated down to 1/10th for the cellulosic fermentor and hemicellulose fermentor by removing the permeate. The cell mass produced at the end of batch fermentation of 1.5 g/L dry cell weight was concentrated to 15 g/L to start continuous fermentation.

After the transfer and concentration, a continuous fermentation was initiated by feeding fresh production medium components separately from sugar stock as shown on FIG. 1. The sterile water was fed separately to the desired media strength. The inflow of the feeding medium was balanced by an outflow of permeate from the membrane module, while recycling cells. The culture pH was controlled at 4.8 by addition of aqueous ammonia solution during the acidogenic phase, and was not controlled when it became higher than the set value during the solventogenic phase.

The liquid-liquid extraction (LLX) of cell-free fermentation broth was conducted using butyl butyrate as extractant. The LLX equipment was operated continuously, with a number of organic-to-aqueous (O:A) ratios between 0.5 and 2.2. The raffinate was used to replace water dilution in both fermentors. The samples of feeds, permeate, and raffinate were taken to determine the mass balance around the system.

FIGS. 2A and 2B show fermentation results, where cellulosic hydrolysate was continuously fed 112 h and cells were bled to hemicellulosic hydrolysate for 92 h. The average total solvents produced, productivity and total solvent yield of 112 h continuous operation of $C_6$ fermentor were at 13.5 g/L, 9.1 g/L/h and 0.30 g/g, respectively.

The average of a steady-state operation which was seen as a capacity of the system to perform is shown in Table 1. The performance of $C_6$ hydrolysate in terms of total solvent production, productivity, and solvent yield was comparable or better to dextrose feed in a similar system with continuous membrane-assisted fermentation. The average dilution rate during the steady state was 0.77 per hour. Survase et al. (2011) used the conventional single-stage chemostat culture for continuous production of solvents and found that dilution rates above 0.1/h resulted in significant drop in total solvents as well as cell washout.

During the membrane-assisted cell recycle experiment, the total cell concentration (DCW) was increased and maintained below 50 g/L and the residual glucose concentration was maintained at about 10 g/L. The continuous fermentation of hemicellulosic hydrolysate from pine was initiated using pine cellulosic hydrolysate as feed for the first 20 h. After continuous operation of 20 h, the total solvents reached 13.5 g/L and pine hemicellulosic hydrolysate was fed to the second fermentor until the end of fermentation at 112 h. FIG. 2B shows the continuous production profile of solvents, acids, and DCW where pine hemicellulosic hydrolysate was used as feed. The average total solvents produced, productivity, and total solvent yield of 92 h continuous operation of hemicellulosic fermentor were at 9.4 g/L, 6.3 g/L/h and 0.43 g/g, respectively. The average dilution rate during the steady state was 0.68/h. Xylose utilization averaged 45% of the feed in one pass. The results as a capacity of the system to perform are shown in Table 2.

TABLE 2

Summary of Results of Example 4.

| Fermentation Parameter | Runtime average (112 h) | Runtime average (92 h) |
|---|---|---|
| Total ABEI, g/L | 13.5 | 9.4 |
| Butanol, g/L | 7.7 | 5.3 |
| Acetone, g/L | 4.3 | 3.0 |
| Isopropanol, g/L | 0.54 | 0.3 |
| Ethanol, g/L | 0.96 | 0.8 |
| Acetic acid, g/L | 1.75 | 1.4 |
| Butyric acid, g/L | 2.1 | 2.2 |
| Productivity, g/L/h | 9.1 | 6.3 |
| Yield, g/g of utilized sugar | 0.30 | 0.43 |
| Utilized sugars in one pass, % | 77 | 72 |
| Dilution rate, per h | 0.70 | 0.6 |

FIG. 3 shows a summary of the selectivity of each solvent component at different O:A feed mass ratios during the continuous forward extraction performance. The recovery of butanol from the membrane permeate consistently exceeded 90% with average recovery greater than 95% in all the O:A ratios explored. The concentration of butyl butyrate extractant in the raffinate averaged 0.40 g/L, which translates into loss of less than 0.1% of the extractant used in LLX. There was no observed inhibition from butyl butyrate recycled in raffinate on the fermentation performance. The pilot run also demonstrated that the percentage of raffinate (20-74%) used in the fermentation broth had no adverse effect on fermentation.

Example 5

The bench-scale LLX system was used to study liquid-liquid equilibrium of the selected solvents produced by Clostridium fermentation. Butyl butyrate (containing 0.035 g/L butanol, obtained from ParChem) was utilized as extractant. At the investigated extraction conditions (1:1 O:A ratio, 50° C. and pH 3.8 or 37° C. and pH 4.8), high solvent recovery for butanol (95-97%), acetone (98-99%), and isopropanol (92-96%) was achieved. It was found that the equilibrium for butanol reached after three steps because of its highest partition coefficient among all the solvents (Tables 3 and 4). Ethanol had a relatively low partition coefficient of 0.23, which resulted in a low recovery of about 60%. The ethanol recovery can be improved to 70% by increasing the O:A ratio to 3.5-4. The extraction of acids was found mainly dependent on the pH of fermentation broth. The lower pH favored extraction of acids, whereas at pH of 4.8, the acetic acid and butyric acid extraction efficiency was only 12-15% after six stages.

TABLE 3

Solvent Partition Coefficient and Required Butyl Butyrate:Feed Ratio.

| Compound | Partition coefficient | Minimum Butyl butyrate:feed ratio |
| --- | --- | --- |
| Butanol | 5.62 | 0.18 |
| Acetone | 1.10 | 0.91 |
| Ethanol | 0.23 | 4.35 |
| Isopropanol | 0.71 | 1.41 |
| Acetic acid | 0.11 | 9.09 |
| Butyric acid | 2.66 | 0.38 |

TABLE 4

Solvent Recovery (%) for 6-Step Cross-Current LLX at pH 4.8 and 37° C. Using Butyl Butyrate.

| No. of LLX Steps | Butanol | Acetone | Ethanol | Isopropanol | Acetic acid | Butyric acid |
| --- | --- | --- | --- | --- | --- | --- |
| Step I | 77 | 53 | 17 | 37 | 4 | 41 |
| Step II | 90 | 69 | 26 | 55 | 7 | 11 |
| Step III | 96 | 83 | 36 | 70 | 10 | 14 |
| Step IV | 97 | 91 | 46 | 80 | 12 | 16 |
| Step V | 97 | 95 | 51 | 86 | 14 | 17 |
| Step VI | 97 | 98 | 59 | 92 | 16 | 14 |

Example 6

In this example, pine cellulosic hydrolysate was fed in parallel with pure xylose, as well as conditioned pine hemicellulosic hydrolysate. During these runs, the raffinate was fed after a 30 h initial period of continuous fermentation. The composition and treatment was the same as in Example 1.

Figure 4A:
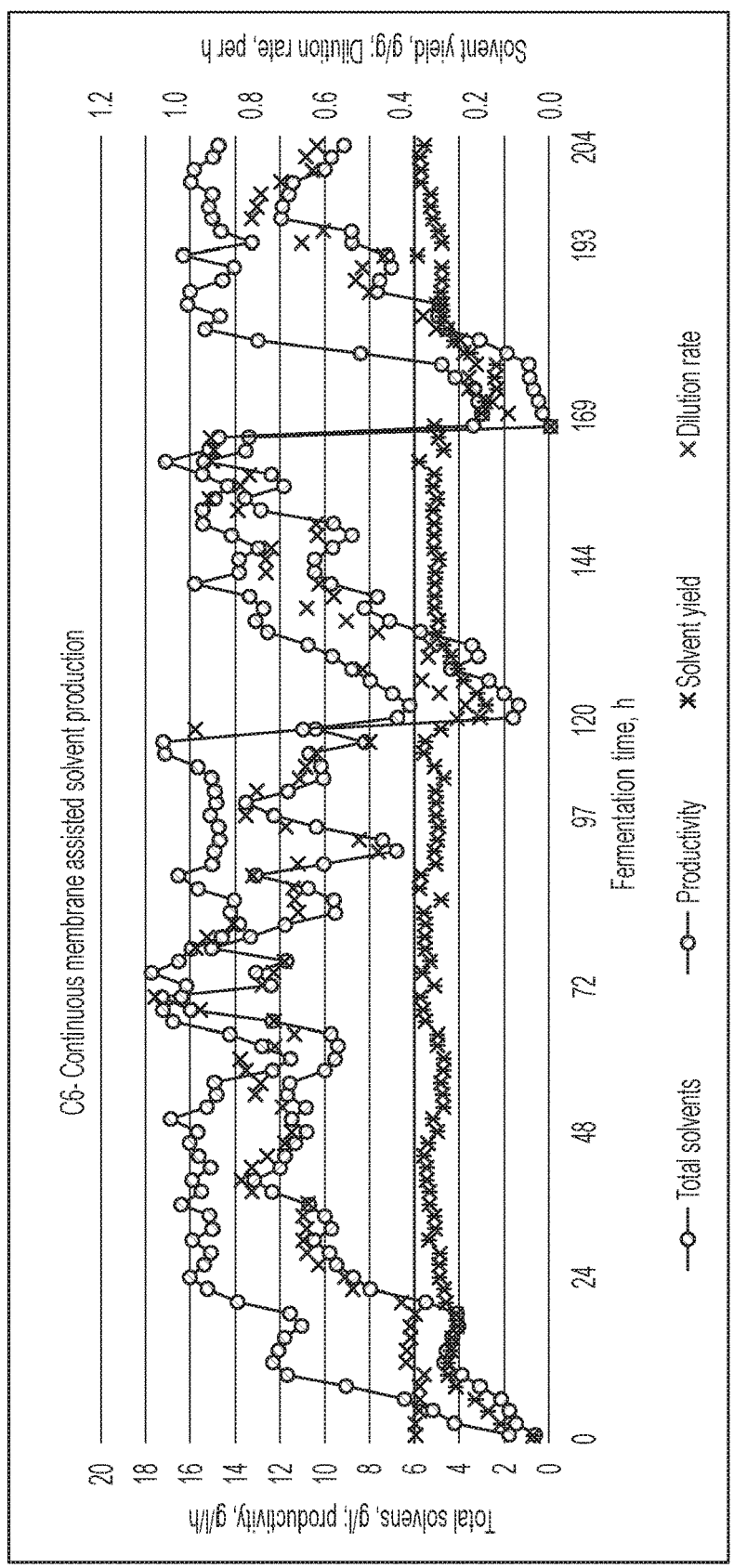
FIG. 4A shows fermentation performance for the $C_6$-rich fermentor, in Example 6.
Figure 4B:
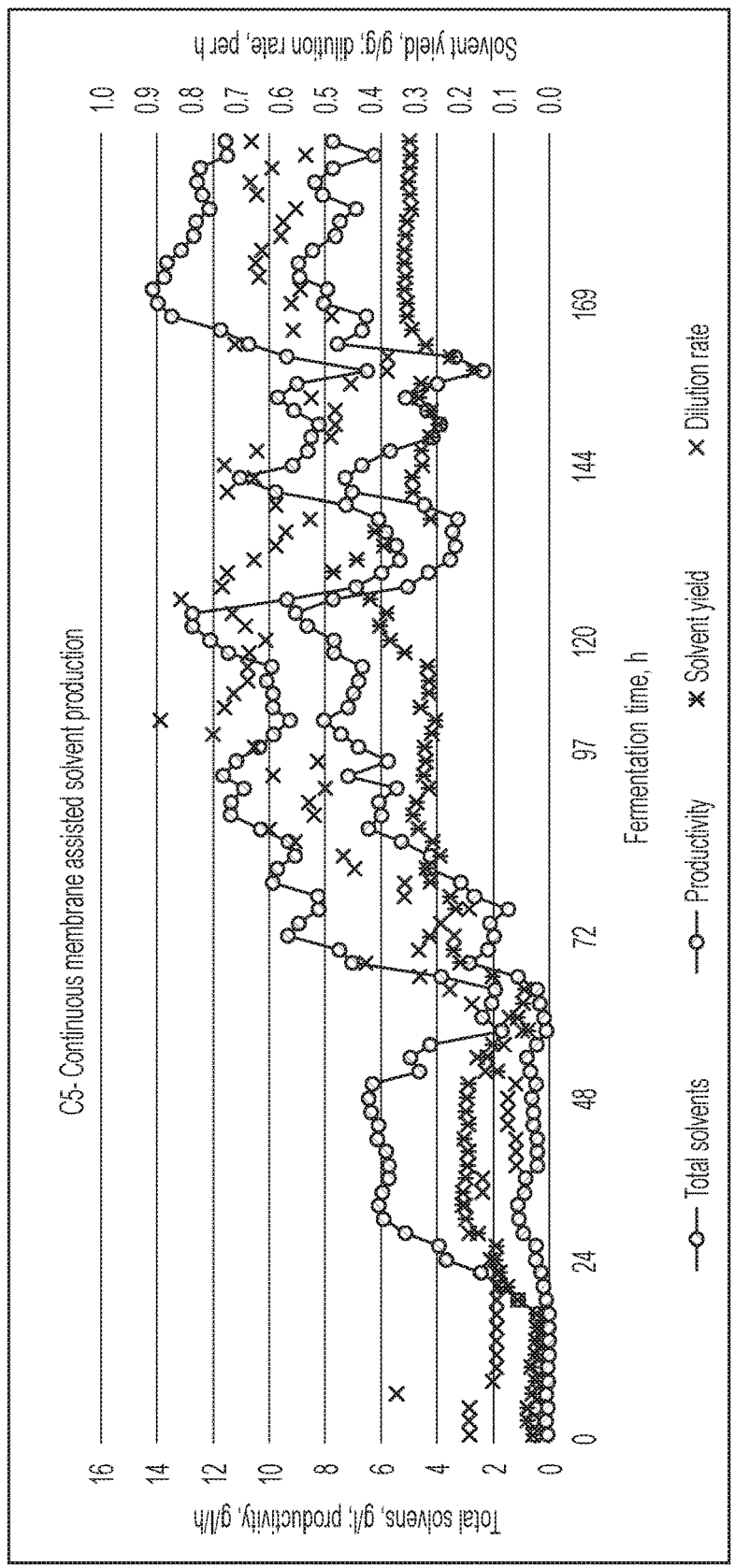
FIG. 4B shows fermentation performance for the $C_5$-rich fermentor, in Example 6.

FIG. 4A ($C_6$-rich fermentor) and FIG. 4B ($C_5$-rich fermentor) show fermentation performance for Example 6. The average total solvents for 100 h of operation with cellulosic hydrolysate was 13.1 g/L, with solvent productivity 7.4 g/L/h, and solvent yield 0.30 g/g. The average total solvents for 100 h of operation with hemicellulosic hydrolysate was 10.1 g/L, solvent productivity 4 g/L/h, and solvent yield 0.4 g/g. The performance of $C_5$ hydrolysate after conditioning treatment was significantly improved from 0.7 g/L/h to 4 g/L/h, with yield of 0.4 g/g. Some improvement in yield can also be attributed to recycle of butyric acid and acetic acid, which are the intermediate byproducts and are not extracted by butyl butyrate at these conditions.

Solvent toxicity and specifically butanol concentration above 10 g/L caused a sharp drop in solvent production. The hemicellulose fermentor was started feeding with dextrose until sufficient cell density was reached, then pure xylose was fed continuously, and finally conditioned hemicellulosic hydrolysate was fermented. The hemicellulosic hydrolysate treated with activated carbon gave results very similar to xylose performance. The xylose feed between 38 h to 70 h of fermentation gave average total solvents 10.7 g/L, total solvent productivity 3.5 g/L/h, and solvent yield 0.30 g/g. This shows that the conditioning of $C_5$ hydrolysate was very efficient to remove possible inhibitors, bringing the performance of $C_5$ hydrolysate similar to synthetic xylose.

Example 7

Corn stover hemicellulosic hydrolysate from sulfur dioxide-ethanol-water pretreatment was obtained before heat treatment to monomer and oligomeric sugars as follows (in g/L): glucan 11.53, xylan 46.2, galactan 6.7, arabinan 8.25, mannan 3.08, acetic acid 1.63, formic acid 1.02, levulinic acid 0.17, hydroxymethylfurfural 0.06, furfural 0.07, and lignosulfonate 28.6.

The hemicellulosic hydrolysate was conditioned. The conditioning incorporated liming for pH adjustment to 6.0 and settling, centrifugation of sludge, membrane ultrafiltration of supernatant and centrate, diafiltration of retentate from ultrafiltration, and optional activated carbon treatment. The total sugar loss was to 9.8%. Table 5 gives the sugar recovery from each step.

TABLE 5

Sugar Recovery From Each Step of Conditioning in Example 7.

| Product Stream | % Sugar Recovery |
| --- | --- |
| Hydrolysate (end of autohydrolysis) | 100.0 |
| Hydrolysate (limed) | 96.9 |
| Supernatant and Centrate | 95.8 |
| Permeate | 90.2 |
| Retentate | 3.9 |

Maximizing total sugar recovery was combined with a parallel objective to minimize the amount of inhibitors that are present in the hydrolysate feed to Clostridium fermentation. Table 6 summarizes the % total removal of fermentation inhibitors after conditioning of hemicellulosic hydrolysate. Approximately 50% or more of major inhibitors were removed. Formic acid, a major Clostridium fermentation inhibitor, was reduced by 68%, largely owing to liming. About half of lignosulfonate i.e. soluble lignin present in hemicellulosic hydrolysate, was removed by liming which contributed to 28% of removal and ultrafiltration accounted for another 20%. Both 5-HMF and furfural were reduced by about 60% after hemicellulosic sugar conditioning, and liming was the main driver for their reduction. Acetic acid and levulinic acid were not removed to an extent that is comparable to those of the major inhibitors.

TABLE 6

Removal of Fermentation Inhibitors During Corn Stover $C_5$ Hydrolysate Conditioning.

| Inhibitors in Permeate | % Fermentation Inhibitor Removal |
|---|---|
| Formic Acid | 68.2 |
| Acetic Acid | 2.1 |
| Levulinic Acid | 17.5 |
| 5-HMF | 59.9 |
| Furfural | 62.1 |
| Lignosulfonate (soluble lignin at 280 nm) | 48.1 |

Example 8

A hemicellulosic fermentor was started with dextrose for the first 24 h to grow cell density, and then followed by xylose and hemicellulosic corn stover hydrolysate fermentation. Upon stabilizing, the culture was continuously fed with xylose, followed by alternatively conditioned hemicellulosic hydrolysate in descending order of the conditioning effectiveness. The overlimed $C_5$ hydrolysate with membrane treatment and maximum carbon treatment was fed first. The treatments A, C, E, G, and I were overlimed to pH 10, while treatments B, D, F, H, and J were limed to pH 6 only. The membrane with cutoff at 4000 molecular weight was not used for hydrolysates I and J. Activated Carbon was varied, at 1:1, 1:2, and 1:4 ratio on sugar to none for hydrolysates G, H, I, and J, respectively.

The performance of various hydrolysates in parallel fermentation with cell bleed from dextrose-fed fermentor is summarized in Table 7. No raffinate was recycled for this experiment. Table 7 shows the average total solvents, productivity, yield, and specific productivity for all the hemicellulosic hydrolysates. The specific productivity considers the dry cell weight (DCW) accumulation over the period of time.

TABLE 7

Average Solvents, Productivity, Yield, and Specific Productivity in Example 8.

| | Total Solvents, g/L | Productivity, g/L/h | Yield, g/g | DCW, g/L | Specific Productivity, g/L/H/g DCW |
|---|---|---|---|---|---|
| Xylose | 6.07 | 2.99 | 0.24 | 25.0 | 0.12 |
| A | 6.13 | 3.21 | 0.23 | 50.0 | 0.06 |
| B | 10.28 | 6.06 | 0.28 | 75.0 | 0.08 |
| C | 9.07 | 5.33 | 0.30 | 65.0 | 0.08 |
| D | 10.44 | 7.36 | 0.31 | 72.0 | 0.10 |
| E | 12.17 | 9.29 | 0.31 | 80.0 | 0.12 |
| F | 9.87 | 7.08 | 0.32 | 70.0 | 0.10 |
| G | 8.38 | 6.06 | 0.30 | 60.0 | 0.10 |
| H | 8.03 | 5.82 | 0.34 | 85.0 | 0.07 |
| I | 7.75 | 5.67 | 0.36 | 105.0 | 0.05 |
| J | 5.52 | 3.90 | 0.33 | 105.0 | 0.04 |

It was observed that liming and membrane treatment is sufficient with some degree of carbon treatment (up to 0.56 g C/g monosaccharides) preferable to condition the hemicellulosic hydrolysate. The membrane treatment was found to be an important step to remove inhibitors from $C_5$ hydrolysate. The conditioned sugar specific productivity for hydrolysate E was similar to pure xylose.

REFERENCES

Afschar, A. S., Biebl, H., Schaller, K., Schügerl, K., 1985. "Production of acetone and butanol by *Clostridium acetobutylicum* in continuous culture with cell recycle." *Appl. Microbiol. Biotechnol.* 22, 394-398.

Bankar, S. B., Jurgens, G., Survase, S. A., Ojamo, H., Granström, T. 2015. "Genetic engineering of *Clostridium acetobutylicum* to enhance isopropanol-butanol-ethanol production with an integrated DNA-technology approach." *Renewable Energy*, 83, 1076-1083.

Bankar, S. B., Jurgens, G., Survase, S. A., Ojamo, H., Granström, T. 2014. "Enhanced isopropanol-butanol-ethanol (IBE) production in immobilized column reactor using modified *Clostridium acetobutylicum* DSM792." *Fuel*, 136, 226-232.

Barton, W. E., Daugulis, A. J. 1992. "Evaluation of solvents for extractive butanol, fermentation with *Clostridium acetobutylicum* and the use of poly(propylene glycol) 1200." *Appl. Microbiol. Biotechnol.* 36, 632-639.

Busche R. M. 1991. "Techno economic evaluation of the extractive fermentation of butanol as a guide to research in this area of biotechnology." [www.osti.gov/scitech/biblio/10106632]

Cai, D., Hu, S., Miao, Q., Chen, C., Chen, H., Zhang, C., Li, P., Qin, P., Tan T. 2017. "Two-stage pervaporation process for effective in situ removal acetone-butanol-ethanol from fermentation broth." *Bioresour. Technol.* 224, 380-388.

Cai, D., Wang, Y., Chen, C., Qin, P., Miao, Q., Zhang, C., Li, P., Tan T. 2016. "Acetone-butanol-ethanol from sweet sorghum juice by an immobilized fermentation-gas stripping integration process." *Bioresour. Technol.*, 211, 704-710.

Chen, C. K., Blaschek, H. P. 1999. "Effect of acetate on molecular and physiological aspects of *Clostridium beijerinckii* NCIMB 8052 solvent production and strain degeneration." *Appl. Environ. Microbiol.* 65(2), 499-505.

Davison, B. H., Thompson, J. E. 1993. "Continuous direct solvent extraction of butanol in a fermenting fluidized bed reactor with immobilized *Clostridium acetobutylicum.*" *Appl. Biochem. Biotechnol.* 39 (40), 415-426.

Ennis, B. M., Maddox, I. S., 1989. "Production of solvents (ABE fermentation) from whey permeate by continuous fermentation in a membrane bioreactor." *Bioprocess Eng.* 4, 27-34.

Ferras, E., Minier, M., Goma, G., 1986. "Acetonobutylic fermentation: improvement of performances by coupling continuous fermentation and ultrafiltration." *Biotechnol. Bioeng.* 28, 523-533.

Gapes, J. R., Nimcevic, D., Friedl, A. 1996. "Long-term continuous cultivation of *Clostridium beijerinckii* in a two-stage chemostat with on-line solvent removal." *Appl. Environ. Microbiol.* 62(9), 3210-3219.

Groot, W. J., Soedjak, H. S., Donck, P. B., van der Lans, R. G. J. M., Luyben, K. Ch. A. M.,Timmer, J. M. K. 1990. "Butanol recovery from fermentations by liquid-liquid extraction and membrane solvent extraction." *Biopro. Eng.* 5, 203-216.

Gyamerah, M., Glover J. 1996. "Production of ethanol by continuous fermentation and liquid-liquid extraction." *J. Chem. Technol. Biotechnol.* 66(2), 145-152.

Huang, W. C., Ramey, D. E., Yang, S. T., 2004. "Continuous production of butanol by *Clostridium acetobutylicum* immobilized in a fibrous bed bioreactor." *Appl. Biochem. Biotechnol.* 115, 887-898.

Jiang, W., Yang, S.-T. 2013. "The effects of NADPH reducing power on isopropanol production in *Clostridium Tyrobutyricum.*" 13th AIChE Annual Meeting, San Francisco Calif., USA.

Lee, S-M., Cho. M. O., Park, C. H., Chung, Y.-C., Kim, J. H., Sang, B.-I., Um, Y. 2008. "Continuous butanol production using suspended and immobilized *Clostridium beijerinckii* NCIMB 8052 with supplementary butyrate." *Energy Fuels*, 22 (5), 3459-3464.

Lienhardt, J., Schripsema, J., Qureshi, N., Blaschek, H. P. 2002. "Butanol production by *Clostridium beijerinckii* BA101 in an immobilized cell biofilm reactor: Increase in sugar utilization." *Appl. Biochem. Biotechnol.* 98-100, 591-598.

Mariano, A. P., Qureshi, N., Filho, R. M., Ezeji T. C. 2012. "Assessment of in situ butanol recovery by vacuum during acetone butanol ethanol (ABE) fermentation." *J. Chem. Technol. Biotechnol.* 87(3), 334-340.

Ni, Y., Xia, Z., Wang, Y., Sun Z. 2013."Continuous butanol fermentation from inexpensive sugar-based feedstocks by *Clostridium saccharobutylicum* DSM 13864." *Bioresour. Technol.* 129, 680-685.

Nimcevic, D., Gapes, J. R. 2000. "The Acetone-Butanol Fermentation in pilot plant and pre-industrial scale", *J. Mol. Microbiol. Biotechnol.* 2(1), 15-20.

Pierrot, P., Fick, M., Engasser, J. M., 1986. "Continuous acetone-butanol fermentation with high productivity by cell ultrafiltration and recycling." *Biotechnol. Lett.* 8, 253-256.

Qureshi, N. A., Maddox I. S. 1995. "Continuous production of Acetone-Butanol-Ethanol using immobilized cells of *Clostridium acetobutylicum* and integration with product removal by liquid-liquid extraction." *J. Ferm. Bioeng.* 80(2), 185-189.

Qureshi, N., Schripsema, J., Lienhardt, J., Blaschek, H. P., 2000. "Continuous solvent production by *Clostridium beijerinckii* BA101 immobilized by adsorption onto brick." *World J. Microbiol. Biotechnol.* 16, 377-382.

Schaffer, D. "Small ethanol plants struggle for an edge," *Star Tribune, Mar.* 5, 2015. [www.startribune.com/small-ethanol-plants-struggle-for-an-edge/294436781]

Survase, S. A., Jurgens, G., van Heiningen, A., Granström, T. 2011. "Continuous production of isopropanol and butanol using *Clostridium beijerinckii* DSM 6423." *Appl. Microbiol. Biotechnol.* 91, 1305-1313.

Survase, S. A., Sklavounos, E., Jurgens, G., van Heiningen, A., Granström, T., 2011. "Continuous acetone-butanol-ethanol fermentation using SO2-ethanol-water spent liquor from spruce." *Bioresour. Technol.* 102 (23), 10996-11002.

Survase, S. A., van Heiningen, A., Granström, T., 2012. "Continuous bio-catalytic conversion of sugar mixture to acetone-butanol-ethanol by immobilized *Clostridium acetobutylicum* DSM 792." *Appl. Microbiol. Biotechnol.* 93, 2309-2316.

Tanaka, S., Tashiro, Y., Kobayashi, G., Ikegami, T., Negishi, H., Sakaki K., 2012. "Membrane-assisted extractive butanol fermentation by *Clostridium saccharoperbutylacetonicum* N1-4 with 1-dodecanol as the extractant." *Bioresour. Technol.* 116, 448-452.

Tashiro, Y., Takeda, K., Kobayashi, G., Sonomoto, K., 2005. "High production of acetone-butanol-ethanol with high cell density culture by cell-recycling and bleeding." *J. Biotechnol.* 120, 197-206.

van Heiningen, A., Iakovlev, M., Yamamoto, M., Sklavounos, E., Melin, K., Granstrom, T. "Which fractionation process can overcome the techno-economic hurdles of a lignocellulosic biorefinery?" AIChE Annual Meeting, Minneapolis, 2011.

Vasconcelos, I., Girbal, L., Soucaille, P. 1994. "Regulation of carbon and electron flow in *Clostridium acetobutylicum* grown in chemostat culture at neutral pH on mixtures of glucose and glycerol." *J. Bacteriol.* 176, 1443-1450.

Ventura, J. S., Jahng, D. 2013. Improvement of butanol fermentation by supplementation of butyric acid produced from a brown alga. *Biotechnol. Biopro. Eng.* 18(6), 1142-1150.

Wang, Y., Li X., Blaschek H. P. 2013. "Effects of supplementary butyrate on butanol production and the metabolic switch in *Clostridium beijerinckii* NCIMB 8052: genome-wide transcriptional analysis with RNA-Seq." *Biotechnol. Biofuels.* 6, 138-150.

Xue, C., Liu, F., Xu, M., Tang, I-C., Zhao, J., Bai, F., Yang, S.-T. 2016. Butanol production in acetone-butanol-ethanol fermentation with in situ product recovery by adsorption *Bioresour. Technol.* 219, 158-168.

Yanowitz, J., Christensen, E., McCormick, R. L. 2011. Utilization of renewable oxygenates as gasoline blending components, Technical Report NREL/TP-5400-50791.

Zverlov, V. V., Berezina, O., Velikodvorskaya, G. A., Schwarz, W. H. 2006. Bacterial acetone and butanol production by industrial fermentation in the Soviet Union: use of hydrolyzed agricultural waste for biorefinery. *Appl. Microbiol. Biotechnol.* 71, 587-597.

*Fueling a Nation Feeding the World*, Renewable Fuels Association Publication, 2014. [http://ethanolrfa.org/wp-content/uploads/2015/09/RFA-White-Paper-Fueling-a-Nation-Feeding-a-World.pdf]

Dodds, D., "C5 and C6 sugars—chemistry, not biology." ABLC March Madness Presentation, Apr. 7, 2017. [www.biofuelsdigest.com/bdigest/2017/04/10/chemistry-not-biology-the-digests-multi-slide-guide-to-c5-and-c6-sugars]

What is claimed is:

1. A method of fermenting $C_5$ and $C_6$ sugars to one or more fermentation products, said method comprising:
   (a) introducing a $C_6$-rich sugar feed and a first nutrient mixture to a first fermentor;
   (b) introducing a $C_5$-rich sugar feed and a second nutrient mixture to a second fermentor;
   (c) fermenting at least a portion of said $C_6$-rich sugar feed, in the presence of a fermentation microorganism in said first fermentor, to a first fermentation product;
   (d) fermenting at least a portion of said $C_5$-rich sugar feed, in the presence of said fermentation microorganism in said second fermentor, to a second fermentation product;
   (e) continuously or intermittently removing cells of said fermentation microorganism from said first fermentor, to maintain a first-fermentor microorganism cell concentration within a selected range;
   (f) conveying at least a portion of said cells of said fermentation microorganism from step (e) to said second fermentor, and conveying fermentation broth containing nutrients from said first fermentor to said second fermentor, with or without cell separation from said fermentation broth, whereby said second nutrient mixture is supplemented; and (g) continuously or intermittently removing cells of said fermentation microorganism from said second fermentor, to maintain a second-fermentor microorganism cell concentration within a selected range, wherein said second-fermentor microorganism cell concentration is greater than said first-fermentor microorganism cell concentration.

2. The method of claim 1, wherein maintaining said first-fermentor microorganism cell concentration within a selected range controls foaming in said first fermentor.

3. The method of claim 1, wherein maintaining said second-fermentor microorganism cell concentration within a selected range controls foaming in said second fermentor.

4. The method of claim 1, wherein said method is continuous.

5. The method of claim 1, wherein said fermentation microorganism is a bacteria.

6. The method of claim 1, wherein said fermentation microorganism is a yeast.

7. The method of claim 1, wherein said first fermentor is operated aerobically.

8. The method of claim 1, wherein said second fermentor is operated aerobically.

9. The method of claim 1, wherein said cells of said fermentation microorganism from said first fermentor are removed with a membrane in step (e).

10. The method of claim 1, wherein said cells of said fermentation microorganism from said second fermentor are removed with a membrane in step (g).

11. The method of claim 1, wherein step (f) further includes conveying fermentation broth containing nutrients from said first fermentor to said second fermentor, with cell separation from fermentation broth, wherein all of said second nutrient mixture consists of said fermentation broth containing nutrients from said first fermentor.

12. The method of claim 1, wherein said first nutrient mixture is selected to control said first-fermentor microorganism cell concentration.

13. The method of claim 1, wherein said second nutrient mixture is selected to control said second-fermentor microorganism cell concentration.

14. The method of claim 1, wherein said selected range of said first-fermentor microorganism cell concentration is from about 10 g/L to about 75 g/L (cell dry weight per liter of fermentation broth).

15. The method of claim 14, wherein said selected range of said first-fermentor microorganism cell concentration is from about 20 g/L to about 50 g/L (cell dry weight per liter of fermentation broth).

16. The method of claim 1, wherein said selected range of said second-fermentor microorganism cell concentration is from about 20 g/L to about 100 g/L (cell dry weight per liter of fermentation broth).

17. The method of claim 16, wherein said selected range of said second-fermentor microorganism cell concentration is from about 25 g/L to about 75 g/L (cell dry weight per liter of fermentation broth).

18. The method of claim 1, wherein said first fermentation product is the same as said second fermentation product.

19. The method of claim 1, wherein said first and second fermentation products are selected from the group consisting of alcohols, organic acids, polyols, aldehydes, ketones, hydrocarbons, proteins, enzymes, and combinations thereof.

20. The method of claim 19, wherein said first and second fermentation products include a combination of acetone, n-butanol, and ethanol.

21. The method of claim 19, wherein said first and second fermentation products include a combination of isopropanol, n-butanol, and ethanol.

22. The method of claim 19, wherein said first and second fermentation products include one or more $C_2$-$C_8$ alcohols.

23. The method of claim 19, wherein said first and second fermentation products include one or more acids selected from the group consisting of acetic acid, butyric acid, lactic acid, succinic acid, and combinations thereof.

* * * * *